United States Patent [19]

Fuentes

[11] Patent Number: 5,747,462
[45] Date of Patent: May 5, 1998

[54] PHARMACEUTICALLY ACTIVE COMPOUNDS AND THEIR USE

[75] Inventor: Victoria M. Fuentes, Santiago, Chile

[73] Assignee: Laboratorio CHile S.A., Santiago, Chile

[21] Appl. No.: 516,009

[22] Filed: Aug. 16, 1995

[51] Int. Cl.$^6$ .................... A61K 35/78; A61K 31/70; C07H 1/08
[52] U.S. Cl. .................... 514/23; 514/646; 514/885; 514/886; 514/783; 424/195.1; 536/4.1; 536/127; 536/128
[58] Field of Search .................... 514/23, 646, 885, 514/886, 783; 424/195.1; 536/4.1, 127, 128

[56] References Cited

FOREIGN PATENT DOCUMENTS 2156197  2/1996  Canada.

OTHER PUBLICATIONS

McGarvie et al. *Carbohydrate Research*, vol. 94(1): 67–71, 1981.
Pickett et al. *Am. J. Bot.*, vol. 66(6):618–25, 1979.
Kircher, H. *Phytochemistry*, vol. 16(7): 1078–1080, 1977.
Mindt et al. *J. Sci. Food Agric.*, vol. 26(7):993–1000, 1975.

*Primary Examiner*—John Kight
*Assistant Examiner*—Howard C. Lee
*Attorney, Agent, or Firm*—Graham & James LLP

[57] ABSTRACT

The present invention relates to the area of pharmacology; its objective is to solve the technical problem of inflammation, pain, pruritus and local hyperthermia in human beings and animal species. The composition and the subcompositions thereof are obtained from plants of the family Cactaceae, the main methodological steps being a set of processes: production, purification, physicochemical quantification, biotherapeutic evaluation, biopharmaceutical formulation and molecular identification. From the molecular identification a set of molecules is recognized, comprising carbohydrates and an aromatic amine, the general formulae of which are:

$C_5H_{10}O_5$ (RIBOSE), $C_6H_{12}O_5$ (FUCOSE), $C_6H_{12}O_6$ (GALACTOSE; MANNOSE; GLUCOSE), $C_8H_{11}O_2N$ (1-HYDROXY-1-(4-HYDROXYPHENYL)-2-AMINOETHANE), $C_{10}H_{18}O_9$ (RIBOFURANOSYLRIBOSE).

18 Claims, No Drawings

PHARMACEUTICALLY ACTIVE COMPOUNDS AND THEIR USE

BACKGROUND OF THE INVENTION

The main object of pharmacology, together with biopharmacy, is the search for therapeutic solutions for treating the causes and effects or symptoms which characterize the various pathologies; consequently any drug, medicinal product or novel application which tackles this major objective and its industrial use is an invention. If the novel industrial application is established within a technical/ economic and financial framework, the result is a viable invention whose benefits, besides affecting the technical and economic sphere, make a real contribution to the well-being and quality of life of living creatures.

Anti-inflammatory, analgesic and antipyretic drugs are a heterogeneous group of often unrelated compounds, though almost all are organic acids or corticoids, which share some therapeutic actions and side effects (Flórez J., Armijo J. A., Mediavilla A., 1992; Drug Information, 1995). Recently, considerable progress has been made in elucidating the mechanism of action of these drugs, making it possible to put forward a hypothesis as to why such heterogeneous agents often have the same side effects and the same basic therapeutic activities. In actual fact, the therapeutic activity appears to depend in large measure on the inhibition of a defined biochemical pathway, responsible for the biosynthesis of prostaglandins and of related autacoids (Goodman and Gilman, 1991; Velo G. P. et al., 1980).

Although it is difficult to offer a good physiopathological description of the inflammatory phenomenon in terms of underlying cellular events in the damaged tissue, the phenomenon could be described by means of a succession of events which begin with fenestration of the microscopic vessels, which is followed by filtration of the blood elements into the interstitial spaces and lastly by migration of leukocytes to the inflamed tissue. At macroscopic level, all of this is generally accompanied by the known clinical signs: erythema, edema, hypersensitivity and pain (Goodman and Gilman, 1991; Velo G. P. et al., 1980).

During this complex response, chemical mediators such as histamine, 5-hydroxytryptamine (5-HT), slow-reacting substance of anaphylaxis (SRS-A), various chemotactic factors, bradykinin and prostaglandins are released locally. Phagocytic cells emigrate to the area, and rupture of cellular lysosomal membranes with release of lytic enzymes may occur. All these events may contribute to the inflammatory response.

However, drugs derived from salicylates have little or no effect on the release or activity of histamine, 5-HT, SRS-A or the lysosomal enzymes, and likewise potent antagonists of 5-HT or histamine have little or no therapeutic effect on inflammation; the importance of these mediators in the initiation or maintenance of the inflammatory response may well be doubted. In the particular case of aspirin, it has been demonstrated that the latter has an effect of decreasing the rate of prostaglandin synthesis, by inhibiting a vital enzyme of the process.

The process of inflammation in rheumatoid arthritis patients is rather different, and probably involves the combination of an antigen (gamma globulin) with an antibody (rheumatoid factor) and complement, causing the local release of chemotactic factors which attract leukocytes. These leukocytes phagocytose the antigen-antibody complexes and complement, and also release the many enzymes contained in their lysosomes. These lysosomal enzymes then damage the cartilage and other tissues, increasing the degree of inflammation. Cell-mediated immune reactions may also be involved. Notwithstanding the foregoing, it is important to stress that, during this process, together with the chemotactic factors, prostaglandins are also released.

The effects produced by intradermal, intravenous or intraarterial injections of prostaglandins are strongly reminiscent of the inflammatory process. Prostaglandin $E_2$ ($PGE_2$) and prostacyclin $I_2$ ($PGI_2$), probably generated in nanogram amounts during inflammation, cause erythema and increase local blood flow. The prostaglandins of the E series display, moreover, two important vascular effects which are not generally common to other mediators of inflammation: a long-lasting vasodilator action and a capacity to counteract the vasoconstrictor effects of substances such as noradrenaline and angiotensin. The erythema induced by the intradermal injection of prostaglandin clearly illustrates its prolonged action (up to 10 hours). In contrast, the vasodilatation produced by prostaglandins on the skin vessels and superficial veins disappears after a few minutes.

The migration of leukocytes to the inflamed area is an important aspect of the inflammatory effect. The extent to which prostaglandins contribute to this event has not been resolved. According to some investigators, several prostaglandins attract white cells to the damaged area, thereby initiating the recovery process. This would endow them with a chemotactic character. In spite of this, 12-hydroxyarachidonic acid (HETE) is recognized as the main chemotactic product of arachidonic acid metabolism, and this is not blocked in its synthesis by anti-inflammatories such as indomethacin and salicylic derivatives.

There are also investigators who are attempting to tackle the problem of inflammation by inhibiting the synthesis of interleukin-1 or its action directly, by means of binding of a drug to a particular receptor. Interleukin-1 is known to induce prostaglandin production in cells and to initiate a cascade of events which may result in the production of several other mediators of inflammation, such as leukotrienes and PAF (platelet activation factor). Accordingly, intervening in interleukin-1 synthesis affords a higher probability of holding back the inflammatory process. If the chain of events is mediated by prostaglandins, it will be held back, but the process will also be blocked if the inflammation is mediated by leukotrienes or PAF.

Another strategy which is currently being studied is NOT to inhibit cytokine and lymphokine synthesis directly, but the consequence thereof. According to Dr. Howard Grey, Research Director at the company CYTEL, La Jolla, Calif., a very important consequence of interleukin-1 secretion is the induction of certain molecules at the endothelial surface which are very important in the attraction, adhesion and extravasation of leukocytes to the site of inflammation. In his company, they are attempting to interfere with the interaction between said molecules of the LEC-CAM lectin type, which occur at the surface of endothelial cells or in leukocytes, and the target cells. LEC-CAMs have specificity for carbohydrate type molecules.

This is of great importance, in that a few simple oligosaccharides, stereospecific carbohydrates, could have sufficiently high affinity to be capable of interfering physiologically with the interaction between LEC-CAM-binding cells and their carbohydrate ligands, achieving inhibition of the inflammatory process and avoiding the potential problems of toxicity which manifest themselves when cytokines are inhibited directly.

Pain is another poorly understood physiological process. The greatest advance regarding pain in the last century has been the identification of the neurotransmitters which act in the reaction of the nervous system. There are known to be two phases in the painful process: an ascending phase and a descending phase. Two of the most important neurotransmitters isolated are serotonin and enkephalin, the latter being similar to the endorphins, organic substances which the body secretes normally, which bear great similarity to morphine and which produce the same calming effect as the latter. The mode of action of analgesic agents is not clear either. In the case of the analgesic action of salicylic derivatives against migraines, one of the world's greatest experts in pain research, Dr. Clifford Rose, director of the Academic Neuroscience Unit of Charing Cross & Westminster Medical School, is of the opinion that this is due fundamentally to an action at neurotransmitter level. It apparently participates in the first step of the painful process, preventing it from following its ascending pathway.

There are also findings which give prostaglandins a role in the pain process. Pain may be induced experimentally, and it has been observed that the administration of milligrams of $PGE_2$ and $PGF_{2alpha}$ to women by intramuscular or subcutaneous injection to induce abortion cause intense local pain. Prostaglandins can also cause headaches and vascular pain when infused intravenously in man. Although the doses of prostaglandins for producing pain are high in comparison with the concentrations expected in vivo, the induction of hyperalgesia appears to be a typical response to low concentrations of prostaglandins.

Long-lasting hyperalgesia occurs when very small amounts of $PGE_1$ are administered intradermally to man. Moreover, in human experiments in which separate subdermal infusions of $PGE_1$, bradykinin or histamine, or a mixture of bradykinin and histamine, did not cause frank pain, great pain was experienced when $PGE_1$ was added to bradykinin or to histamine. When $PGE_1$ was infused with histamine, pruritus was noted.

In agreement with this last finding, all those biological factors which participate in the inflammatory process are also present in the pain process, and accordingly a pharmacological action of inhibition of said molecules, synthesis of prostaglandins and associated cofactors, involves a decrease both in inflammation and in pain.

Glycobiology, the science which studies sugar chemistry and its relationship to the science of life, has opened up a new theoretical perspective in the pharmacological debate of the end of the century. This new perspective involves a series of hypotheses which expect to be confirmed by the making of new discoveries of molecular structures which decipher the codes established at levels almost of glycobiological abstraction, to be transformed into tangible answers through the generation of new drugs whose key is determined by their great versatility, heterogeneity and stereospecificity, features which are defined in the family of carbohydrates and associations thereof.

The theory of the so-called "Cell Recognition" mechanism, wherein surface sugars make recognition signals for other cells, has been elucidated in part on verifying the existence of some sugars as mediators of toxin-cell, virus-cell, bacterium-cell and cell-cell cellular coupling mechanisms; but there still exists a theoretical problem which is unsolved, and which serves as a basis for the invention which has been developed, in which attention is drawn to the existence of biological mediators which initiate and trigger the process of inflammation, these mediators being recognized as carbohydrates and associations thereof. The argument postulates that, if there existed a group of chemical compounds with molecular structures similar to carbohydrates and with a very high stereospecificity for the cell receptors, these molecules would block the cascade of fast and slow biochemical reactions which initiate the process of inflammation and pain; accordingly, any drug which resolves this issue would be providing a novel approach to this proposition.

As Nathan Sharon and Halina Lis, in Investigación y Ciencia, March 1993, point out in their article "Carbohydrates in Cell Recognition": "there are cells which position at their surface sugars which make recognition signals for other cells, accordingly medicinal products directed towards these molecules will serve to hold back infection and inflammation", and furthermore, "any drug which blocks the adhesion of leukocytes and their subsequent escape from the blood vessel will enjoy anti-inflammatory properties, consequently the key to the development of such drugs lies in the structure of the binding regions of selectin (selective lectin) molecules and the structure of the carbohydrates where they attach. To seek the maximum efficacy in the anti-adhesive therapy of cell recognition, drugs should be designed or discovered which satisfy a dual objective: to avoid the untimely escape of leukocytes and, on the other hand, to make it easier to leave them in a suitable place".

The mechanism of action which governs the process of cell recognition has been explained by means of the key and lock hypothesis put forward in 1817 by Emil Fischer and improved by various investigators in the present century. The investigations carried out between 1991 and 1994 describe carbohydrates as mediators within the process of cell recognition; these mediators display great molecular diversity and may be combined with one another to form different configurations such as, for example: 4 different monosaccharides could give rise to as many as 35,560 tetrasaccharides; two monosaccharides give rise to 11 different disaccharides, whereas two identical amino acids can generate only one dipeptide; accordingly, in the language of sugars, the words are written not only on the basis of the variety of monosaccharides and the combinations thereof, but also on the basis of the different bonds which join them and of the absence or presence of branching; thereby generating the richest family of combinations of different codes which mediate the biological signals of the mechanism of "key-lock" action in cell recognition, this action being the initiating factor in the cascade of the process of inflammation.

The contemporary therapeutic arsenal for the treatment of inflammation, pain, hyperthermia and pruritus possesses nonsteroidal anti-inflammatory agents, miscellaneous analgesic, antipyretic and anti-inflammatory agents and steroidal anti-inflammatory agents; of basic molecular structure derived from aromatic compounds containing 6 carbon atoms with radicals of the following types: carboxyl or the like, pyrazolone or the like, hydroxyl or the like, propionic or the like, anthranilic or the like, pyrrole or the like; or of complex molecular structure derived from steroids with 21 carbon atoms, designated glucocorticoids, which possess a high molecular weight and a bulky stereospatial structure; these agents satisfy their primary objective, but present two technical problems which have NOT been solved: undesirable concomitant side effects and an appropriate therapeutic window.

Undesirable concomitant side effects at acute and chronic level are, for example: adverse hepatic, renal, cardiovascular, hematological, dermatological, respiratory, immunological (sensitivity reactions and susceptibility to infections), glandular (adrenocorticoid insufficiencies), musculoskeletical, hemodynamic (adverse fluid and electrolyte changes), occular, endocrine, central nervous system and other changes described by the American Hospital Formulary Service in Drug Information of 1995.

The concept of therapeutic window defines the parameters of minimum and maximum dosage which can be administered to a living creature in order to obtain desired therapeutic effects, levels which, when exceeded, exacerbate the concomitant toxic effects and undesirable side effects. The present invention is a preferentially anti-inflammatory and consequently analgesic, local antipyretic and anti-pruritic drug for veterinary and human use, the comparative advantage of which is to afford a therapeutic window with wide and functional margins without causing undesirable concomitant effects and sensitizing, cytotoxic and genotoxic effects at the experimental doses used, and the clinical application of which situates it as a biologically safe and harmless drug of choice.

PREFERENTIAL FIELD OF THE INVENTION

1. PHARMACOLOGY OF ANTI-INFLAMMATORIES, ANALGESICS, LOCAL ANTIPYRETICS AND ANTIPRURITICS, FOR HUMAN AND VETERINARY USE:
i) PHARMACOGNOSY.
ii) PHARMACODYNAMICS.
iii) PHARMACOKINETICS.
iv) PRECLINICAL AND CLINICAL PHARMACOLOGY.
V) PHARMACOTHERAPY.
vi) TOXICOLOGY.
vii) MOLECULAR PHARMACOLOGY.
2. INDUSTRIAL CHEMICAL ENGINEERING:
i) PHARMACEUTICAL TECHNOLOGY.
ii) PHARMACEUTICAL ENGINEERING.
3. BOTANY:
i) PHYTOCHEMISTRY.

DESCRIPTION OF THE INVENTION

New composition and subcompositions of same, consisting of groups of low molecular weight carbohydrate molecules of simple structure, identified as monomers of 5 and 6 carbon atoms of the furanose and pyranose type and a dimer of 10 carbon atoms, composed of all the basic combinations of the monomers, present as D, L, alpha and beta isomeric mixtures, and an aromatic amine of simple structure and low molecular weight, the general formulae of which are: $C_5H_{10}O_5$ (RIBOSE); $C_6H_{12}O_5$ (FUCOSE); $C_6H_{12}O_6$ (GALACTOSE; MANNOSE; GLUCOSE); $C_8H_{11}O_2N$ (1-HYDROXY-1-(4-HYDROXYPHENYL)-2-AMINOETHANE); $C_{10}H_{18}O_9$ (RIBOFURANOSYLRIBOSE); which compositions and subcompositions have high therapeutic potency, do not produce undesirable adverse side effects and are obtained from a species which is amenable to evaluation, from a natural extract originating from a plant of the family Cactaceae, such as, for example, the aerial portion of *Opuntia ovata*, *Opuntia ingenescens*, *Opuntia miquelli* and others, without this ruling out other portions and plants, with anti-inflammatory, analgesic, antipruritic and local antipyretic therapeutic activities in human beings and animals.

PRODUCTION PROCESS OF THE INVENTION: COMPOSITION AND SUBCOMPOSITIONS THEREOF

Methodology for Obtaining the Composition

The methodology for obtaining the COMPOSITION comprises an extraction process from a plant of the family Cactaceae with the object of obtaining a standardized dry extract through steps of sampling and selection using criteria of classification of physical damage, pigmentation and indices of maturity; washing and storage at low temperatures between $-10°$ and $-33°$ C. The first stage of purification involves the steps of conditioning at $5°$ C. for 24 hours and room temperature until the working temperature of between 150 and $20°$ C. is reached; trituration by means of mechanical processes with cutting and impact movements at between 1000 and 5000 rpm; vigorous primary acid digestion under conditions of stirring at between 500 and 1500 rpm and temperature between $40°$ C. and $90°$ C. The filtered solution is neutralized with a solution of hydroxides; it is flocculated with an organic solvent such as acetone and/or lower aliphatic alcohols; it is centrifuged at between 1000 and 2000 rpm and filtered under vacuum. The residue is solubilized in a mixture of water-soluble organic solvents and water in proportions (30:70) to (1:99), the resulting solution is flocculated with organic solvents such as acetone and/or lower aliphatic alcohols, centrifuged at between 1000 and 2000 rpm and filtered under vacuum. The residue thereby obtained is washed on a filter support with organic/aqueous solutions in proportions (80:20) to (99:1); and lyophilized or dried on a fluidized bed, sieving with oscillating systems with retention meshes to obtain a particle size of between 20 and 1000 microns.

The examples which follow provide us with a better understanding of the invention without thereby limiting its field of application.

EXAMPLE 1

The purpose of this example is to show a process for obtaining a standardized dry extract, COMPOSITION, from the aerial portion of plants of the family Cactaceae; the following process was used:

10 selected kilos of vegetable matter from the plant of the family Cactaceae are washed and stored under controlled conditions. The frozen raw material is conditioned for 24 hours at $5°$ C. and 8 hours at room temperature until $18°$ C. is reached and is triturated by cutting at 2000 rpm, and a primary acid digestion is carried out with stirring at 1000 rpm at $50°$ C. for 24 hours with sulfuric acid. The mixture is filtered at low temperature and the solution is neutralized with alkaline hydroxides, flocculated with 20 l of lower aliphatic alcohol, centrifuging at 1230 rpm for 15 minutes, and filtered under vacuum. The flocculate is solubilized with stirring in 10 l of a water/aliphatic alcohol (95:5) solution, and the resulting solution is flocculated with 20 l of lower aliphatic alcohol, centrifuged at 1230 rpm for 15 minutes and filtered under vacuum. The residue is washed on a filter support with organic/water solutions such as aliphatic alcohol/water (95:5), and dried on a fluidized bed at room temperature to obtain a dry extract, which is ground by cutting at high speed with the temperature controlled at $15°$ C. and sieved with oscillating systems to obtain 10 grams of the COMPOSITION with a particle size of between 40 and 500 microns.

EXAMPLE 2

The purpose of this example is to show a process for obtaining a standardized dry extract, COMPOSITION, from the aerial portion of plants of the family Cactaceae; the following process was used:

10 selected kilos of vegetable matter from the plant of the family Cactaceae are washed and stored under controlled conditions. The frozen raw material is conditioned for 24 hours at 5° C. and 8 hours at room temperature until 18° C. is reached and is triturated by cutting at 2000 rpm, and a primary acid digestion is carried out with stirring at 1000 rpm at 60° C. for 24 hours with hydrochloric acid. The mixture is filtered at low temperature and the solution is neutralized with alkaline hydroxides, flocculated with 40 l of lower aliphatic alcohol, centrifuged at 1230 rpm for 15 minutes and filtered under vacuum. The flocculate is solubilized with stirring in 10 l of a water/aliphatic alcohol (95:5) solution, and the solution is flocculated with 40 l of lower aliphatic alcohol, centrifuged at 1230 rpm for 15 minutes and filtered under vacuum. The residue is washed on a filter support with organic/water solutions such as aliphatic alcohol/water or ketone/water (95:5) or aliphatic alcohol/ketone/water (47:47:6), concentrated under reduced pressure and lyophilized to obtain a dry extract, which is ground by cutting at high speed with the temperature controlled at 15° C. and sieved with oscillating systems to obtain 15 grams of the COMPOSITION with a particle size of between 40 and 500 microns.

Methodology for Obtaining the Subcompositions

The methodology for obtaining SUBCOMPOSITIONS from the COMPOSITION comprises the processes of separation and molecular ultraseparation of a standardized dry extract originating from the aerial portion of plants of the family Cactaceae. A sample of the COMPOSITION is hydrated in double-distilled water, stirred for 1 to 2 hours and centrifuged at between 1000 and 2000 rpm for 15 minutes, the insoluble material being separated from the solution. The solution is dialyzed through cellulose and/or cellulose ester membranes with MWCO values below 3500. The dialysis waters are concentrated under reduced pressure, a solid fraction being obtained, and the undialyzed waters (inside the membrane) are concentrated under reduced pressure, a residue being obtained.

The solid fraction is subjected to preparative paper chromatography for 96 hours with solvent systems such as 1-butanol/ethanol/water (4:1:1), 1-butanol/acetic acid/water (6:15:25) and ethyl acetate/pyridine/water (4:10:3). The Subcompositions thereby obtained are eluted with double-distilled water, filtered, concentrated under reduced pressure and lyophilized.

The examples which follow provide us with a better understanding of the invention without thereby limiting its field of application.

EXAMPLE 3

The purpose of this example is to show a process for obtaining SUBCOMPOSITIONS from the COMPOSITION.

10 g of COMPOSITION are solubilized with 2.5 l of double-distilled water with constant stirring for 2 hours. By centrifugation at 1500 rpm for 15 minutes, the insoluble material is separated, 3.87 g being obtained. The solution is dialyzed across a cellulose membrane of MWCO 3500. The dialysis waters are concentrated to dryness under reduced pressure and a solid fraction of 3.34 g is obtained. The undialyzed waters are concentrated to dryness under reduced pressure and a residue of 2.37 g is obtained.

1 g of the solid fraction is subjected to preparative chromatography on Whatman No. 36 paper with a 1-butanol/ethanol/water (4:1:1) solvent system, developing over 100 hours in a descending vertical chamber; separated fractions are obtained, which are eluted with double-distilled water, filtered, concentrated under reduced pressure and lyophilized. The percentages w/w obtained of each subcomposition with respect to the composition are:

first subcomposition: between 1.0% and 5.0%, preferably between 2.0% and 3.0%.

second subcomposition: between 0.5% and 3.0%, preferably between 1.0% and 2.0%.

third subcomposition: between 2.0% and 9.0%, preferably between 3.0% and 5.5%.

fourth subcomposition: between 1.5% and 8.0%, preferably between 2.5% and 5.0%.

PROCESS FOR THE MOLECULAR IDENTIFICATION OF THE COMPOSITION AND SUBCOMPOSITIONS

Process for the Identification of the Composition

The molecular identification processes comprise a set of steps which involve conventional processes for measuring the physicochemical characteristics of the COMPOSITION, such as microscopic description, pH, residues on ignition, water (KF), heavy metals, particle size, solubility, viscosity, FTIR spectroscopy and advanced separation and identification techniques of the chromatographic type such as analytical methodology by HPGLC for identification and quantification of carbohydrates.

The examples which follow provide us with a better understanding of the invention without thereby limiting its field of application.

EXAMPLE 4

The purpose of this example is to show a process for the physicochemical characterization of the COMPOSITION.

1.0 g of COMPOSITION is subjected to the following physicochemical characterization:

Microscopic analysis: amber-yellow granular powder, irregular-shaped crystals between 40 and 800 microns in size are observed. In water, it forms a gelatinous suspension with small dispersed granules. It is partially soluble in alcohol, giving a clear solution and beige-colored particles which settle out.

pH (0.01% solution in hot water)=6.59 pH (0.01% alcoholic solution, hot)=7.30

Water (Karl Fischer)=6.4%

Identity=positive: calcium, phosphate, magnesium and iron

Test for arsenic=: passes USP test

| IR spectroscopy (6% KBr): | | |
|---|---|---|
| 750–800 (cm$^{-1}$) | 50–65% (T) | specific signal |
| 1000–1200 (cm$^{-1}$) | 45–50% (T) | oxygenated substances signal |
| 1300–1350 (cm$^{-1}$) | 43–55% (T) | specific signal |
| 1600–1750 (cm$^{-1}$) | 30–40% (T) | carboxylic substances signal (1740) aromatic substances signal (1620) |
| 3300–3600 (cm$^{-1}$) | 30–55% (T) | specific signal |

The methodology for identification and quantification consists of a process of hydrolysis, reduction, acetylation and HPGLC chromatographic analysis of the hydrolysis products as alditol acetates.

A sample of the composition is hydrolyzed with between 1 and 3N trifluoroacetic acid for 12 to 24 hours at 60°–90° C. The mixture is concentrated to dryness under reduced pressure, washing repeatedly with double-distilled water until a pH of between 4 and 6 is obtained. The hydrolysis products are dissolved in a minimum volume of water. 0.1 g of $NaBH_4$ is added with continuous stirring for 2 to 5 hours at room temperature, and the mixture is neutralized with acid resin and concentrated to dryness under reduced pressure. The reduction products are washed repeatedly with methanol until the borates formed have been removed completely, and dried for 24 hours in a desiccator. The reduced hydrolysis products are dissolved in the minimum volume of anhydrous pyridine and an equal volume of acetic anhydride is added. The excess pyridine is removed under reduced pressure and the products are washed repeatedly with ethanol. The samples are analyzed in a Varian 3700 gas chromatograph, with flame ionization detector, ECNSS-M column on 3% Chromosorb, Hewlett-Packard integrator, with $N_2$ carrier gas at a flow rate of 20 ml/minute, injecting 1 µl, column t° 160°–210° C.

The determination of alditol acetates is carried out by comparison of the retention times with alditol acetate standards under the same conditions and verifying with a cochromatographic technique. The insoluble material is quantified by weighing and identified by FTIR.

The examples which follow provide us with a better understanding of the invention without thereby limiting its field of application.

EXAMPLE 5

The purpose of this example is to show a process for the identification and quantification of low molecular weight carbohydrates present in the COMPOSITION.

0.1 g of COMPOSITION is hydrolyzed with 2 N trifluoroacetic acid for 16 hours at 90° C. The mixture is concentrated to dryness under reduced pressure, washing repeatedly with double-distilled water until the pH is 5. The hydrolysis products are dissolved in a minimum volume of water. 0.1 g of $NaBH_4$ is added with continuous stirring for 2.5 hours at room temperature, and the mixture is neutralized with acid resin and concentrated to dryness under reduced pressure. The reduction products are washed repeatedly with methanol until the borates formed have been removed completely, and are dried for 24 hours in a desiccator. The reduced hydrolysis products are dissolved in the minimum volume of anhydrous pyridine and an equal volume of acetic anhydride is added. The excess pyridine is removed under reduced pressure and the products are washed repeatedly with ethanol. 1.0 µl of the samples is injected under the conditions described above, using injector t°=220° C., detector t°=260, initial column t°=160° C.×3', increment 8° C.×1' and final column t°=210° C.×10', and the following sugars are identified: Fucose (rt=7.04 min, ABC= 20.0%), Galactose (rt=12.94 min, ABC=29.2%), Glucose (rt=13.65 min, ABC=21.3%).

The FTIR spectrum of the insoluble material proves very similar to that of the cellulose standard, recorded under the same conditions. Amount obtained with respect to composition 0.025 g (25% with respect to Composition). Process for the Qualitative Identification of the Subcompositions The SUBCOMPOSITIONS are identified by qualitative chemical tests such as phenol-sulfuric acid, Molisch (alpha-naphthol) and p-anisidine HCl in paper chromatography.

The examples which follow provide us with a better understanding of the invention without thereby limiting its field of application.

EXAMPLE 6

The purpose of this example is to show a process for the qualitative identification of sugars.

1 g of the solid fraction obtained according to the process of Example 3 is subjected to preparative chromatography on Whatman No. 36 paper with a 1-butanol/ethanol/water (4:1:1)=solvent system, developing over 100 hours in a descending vertical chamber; separated fractions are obtained, which are identified with phenol-sulfuric acid, Molisch (alpha-naphthol) and p-anisidine hydrochloride reagents, the following being obtained:

Phenol-sulfuric acid and Molisch=positive for sugars.

p-Anisidine hydrochloride=negative for uronic acids.

Process for the Qualitative and Quantitative Identification of the Subcompositions The SUBCOMPOSITIONS are identified and quantified by means of HPLG techniques as alditol acetates, and NMR techniques with arrangements and contrivances such as $^1H$ 1-D NOESY-presat, 2-D NOESY-presat and TOCSY-presat, COSY, $^{13}C$ NMR and the like, in the following equipment:

NMR-200 for proton $^1H$ and carbon $^{13}C$ resonance,

LC-NMR-500 on flow and stop flow for proton $^1H$ resonance,

NMR-600 for proton $^1H$ resonance,

NMR-750 for proton $^1H$ resonance.

The examples which follow provide us with a better understanding of the invention without thereby limiting its field of application.

EXAMPLE 7

The purpose of this example is to show a process for identifying the molecular structures of SUBCOMPOSITION-1 (SC1) with NMR.

58 mg of SC1 are diluted in a sufficient amount of double-distilled water or water/$D_2O$, and the mixture is shaken until dissolution has taken place, ultracentrifuged and injected directly into the LC-NMR and/or NMR equipment. LC-NMR analyses correspond to fractions separated by HPLC and identified jointly by means of coupling to NMR-500 equipment; on the other hand, direct analyses in NMR equipment correspond to a mixture of compounds of SC1.

1-HYDROXY-1-(4-HYDROXYPHENYL)-2-AMINOETHANE LC-NMR-500 on flow and LC-NMR-500 stop flow, fraction of SC1 with rt=36 min, proton $^1H$ resonance ($^1H$ NMR), spectrum in delta

| aromatic signal | 7.13 ppm | (d, 2H) | |
|---|---|---|---|
| aromatic signal | 6.80 ppm | (d, 2H) | |
| CH signal | 4.58 ppm | (d, 1H) | X part, ABX system, 1H |
| $CH_2$ signal | 3.00 ppm | (m, 2H) | AB part, ABX system, 2H |

For its characterization, additional 1D and 2D experiments in NMR-600 were performed on the SC1 mixture.

GALACTOSE

LC-NMR-500 on flow and LC-NMR-500 stop flow, fraction of SC1 rt=16.04 min, proton $^1H$ resonance ($^1H$ NMR), spectrum in delta

| alpha isomer: | | |
|---|---|---|
| CH signal | 5.29 ppm | (d, 1H) |
| CH signal | 4.30 ppm | (d, 1H) |
| CH signal | 3.90 ppm | (dd, 1H) |

-continued

| CH signal beta isomer: | 3.78 ppm | (dd, 1H) |
|---|---|---|
| CH signal | 4.58 ppm | (d, 1H) |
| CH signal | 4.24 ppm | (d, 1H) |
| CH signal | 3.69 ppm | (dd, 1H) |
| CH signal | 3.47 ppm | (dd, 1H) |

Note:
These spectral signals were obtained from a projection of a two-dimensional spectrum.

For its characterization, additional 1D and 2D experiments in NMR-600 were performed on the SC1 mixture.

MANNOSE

NMR-200 for resonance of carbon decoupled from protons with $^{13}C$ {1H} CPD irradiation.

| alpha-pyran isomer | |
|---|---|
| C1 signal | 96.79 ppm |
| C2 signal | 73.22 ppm |
| C3 signal | 73.00 ppm |
| C4 signal | 70.13 ppm |
| C5 signal | 74.59 ppm |
| C6 signal | 63.41 ppm |
| beta-pyran isomer C1 signal | 96.20 ppm |

There are signals corresponding to the anomeric protons for the beta-pyran compound, and it is present as a less preponderant compound.

EXAMPLE 8

The purpose of this example is to show a process for identifying the structures of SUBCOMPOSITION-2 (SC2) with NMR.

38 mg of SC2 are diluted in a sufficient amount of double-distilled water or water/$D_2O$, and the mixture is shaken until dissolution has taken place, ultracentrifuged and analyzed in NMR. The direct analyses in NMR equipment correspond to a mixture of compounds of SC2.

RIBOSE

NMR-750, proton $^1H$ resonance ($^1H$ NMR), spectrum in delta

| alpha-furan isomer | | |
|---|---|---|
| CH signal | 5.40 ppm | H1 |
| CH signal | 4.10 ppm | H2 |
| CH signal | 4.15 ppm | H3 |
| CH signal | 3.80 ppm | H4 |
| CH signal | — ppm | H5A |
| CH signal | — ppm | H5B |
| beta-furan isomer | | |
| CH signal | 5.25 ppm | H1 |
| CH signal | 4.00 ppm | H2 |
| CH signal | 4.15 ppm | H3 |
| CH signal | 4.00 ppm | H4 |
| CH signal | 3.81 ppm | H5A |
| CH signal | 3.67 ppm | H5B |
| RIBOFURANOSYLRIFOBURANOSE | | |
| NMR-750, proton $^1H$ resonance ($^1H$ NMR), spectrum in delta | | |
| CH signal | 5.42 ppm | (d, 1H) |
| CH signal | 4.22 ppm | (d, 1H) |
| CH signal | 4.06 ppm | (t, 1H) |
| CH signal | 3.90 ppm | (dt, 1H) |
| CH signal | 3.80 to 3.87 ppm | (m, 5H) |
| CH signal | 3.77 ppm | (t, 1H) |
| CH signal | 3.69 ppm | (AB, 2H) |
| CH signal | 3.57 ppm | (dd, 1H) |
| CH signal | 3.48 ppm | (t, 1H) |

The signals correspond to a mixture of monomers and disaccharides in alpha and beta configurations.

EXAMPLE 9

The purpose of this example is to show a process for identifying the structures of SUBCOMPOSITION-3 (SC3) with NMR.

106 mg of SC3 are diluted in a sufficient amount of double-distilled water or water/$D_2O$, and the mixture is shaken until dissolution has taken place, ultracentrifuged and analyzed directly in the NMR equipment. The direct analyses in NMR equipment correspond to a mixture of compound SC3.

| GLUCOSE | | |
|---|---|---|
| NMR-750, proton $^1H$ resonance ($^1H$ NMR), spectrum in delta | | |
| alpha-pyran isomer (34%) | | |
| CH signal | 5.24 ppm | H1 |
| CH signal | 3.54 ppm | H2 |
| CH signal | 3.72 ppm | H3 |
| CH signal | 3.50 ppm | H4 |
| CH signal | 3.83 ppm | H5 |
| CH signal | 3.85 ppm | H6A |
| CH signal | 3.77 ppm | H6B |
| beta-pyran isomer (65%) | | |
| CH signal | 4.65 ppm | H1 |
| CH signal | 3.25 ppm | H2 |
| CH signal | 3.47 ppm | H3 |
| CH signal | 3.41 ppm | H4 |
| CH signal | 3.42 ppm | H5 |
| CH signal | 3.90 ppm | H6A |
| CH signal | 3.73 ppm | H6B | alpha- and beta-furan isomer

There are signals corresponding to the anomeric protons for alpha and beta, they are present as traces.

EXAMPLE 10

The purpose of this example is to show a process for identifying the structures of SUBCOMPOSITION-4 (SC4) with HPGLC as alditol acetates.

0.1 g of SUBCOMPOSITION-4 (SC4) is dissolved in a minimum volume of water, 0.1 g of $NaBH_4$ is added with continuous stirring for 2.5 hours at room temperature, and the mixture is neutralized with acid resin and concentrated to dryness under reduced pressure. The reduction products are washed repeatedly with methanol until the borates formed have been removed completely, and are dried for 24 hours in a desiccator. The reduced hydrolysis products are dissolved in the minimum volume of anhydrous pyridine and an equal volume of acetic anhydride is added. The excess pyridine is removed under reduced pressure and the products are washed repeatedly with ethanol. 1.0 μl of the samples is injected under the conditions described above, using injector t°=220° C., detector t°=260, initial column t°=160° C.×3', increment 8° C.×1' and final column t°=210° C.×10', and the following sugar is identified: Fucose (rt= 7.04 min).

FORMULATION PROCESS AND BIOPHARMACEUTICAL SPECIFICATIONS

The compounds of the invention (Composition and Subcompositions thereof) may be administered in mammals, including human beings, suffering from inflammatory pathologies, with pain, local hyperthermia and/or pruritus, by the administration of a therapeutically effective amount of the Composition, preferably by topical, enteral or parenteral administration. The appropriate daily dose for obtaining this therapeutic effect is approximately 185 and 3 mg/kg body weight for the Composition, although the optimum dose of the compound may be determined by the specialist practitioner considering the patient's age, weight and general state of health. The daily dose may be administered in one or several treatments over a period of time, such as one or several doses per day or using sustained-action preparations.

The active compounds (Composition and Subcompositions) may be administered alone or, more usually, in the form of pharmaceutical compositions which comprise a therapeutically effective amount of the active agent in combination with a carrier or pharmaceutically acceptable inert diluent. The choice of diluent or carrier is determined by the administration route, the solubility of the drug and conventional pharmaceutical practice.

For topical administration, the active ingredients may be formulated as an ointment, paste, gel, lotion, cream or solution, by combining the active agents with a pharmaceutically acceptable inert liquid such as water, or semi-solid such as petroleum jellies, and, where necessary, an emulsifying agent, gelling agent, surfactant, gums and the like, preservatives, using conventional formulation techniques. For example, topical gels containing the active compound (composition or subcompositions) in a gelling hydrophilic base, such as acrylic acid polymers, humectant and emollient agents such as glycerol, propylene glycol, polyethylene glycol 300-400-1000, preservative agents such as parabens, sterile water for injections, and administered topically.

For oral administration, the doses may be prepared according to standard processes, which may contain the active principle alone or formulated as the main active ingredient. A wide variety of solid formulations, such as tablets, troches, coated tablets, dragees, hard capsules, soft capsules, powders and granules, normal or sustained-release, utilize inert excipients such as microcrystalline celluloses, dipac, ditab, lactose, starch, direct-tableting lactose, polyvinylpyrrolidone, talc, magnesium stearate, aerosol, propylene glycol, polyethylene glycols or diluents for sustained action such as waxy matrices, ionic resins, synthetic or natural esters, fats, acrylic films for granulation and/or coating, and the like. For example, uncoated tablets, formulated by a pharmaceutically acceptable dry method, containing 100 mg of active principle designated Composition, prepared according to standard processes in an inert diluent, for example microcrystalline cellulose, ditab, dipac, direct-tableting lactose, lubricants, antiadhesive agents and glidants such as talc, magnesium stearate, polyethylene glycol 6000, and administered orally. Liquid formulations such as syrups, suspensions, elixirs, drops, powders to be reconstituted, which utilize inert excipients such as water and several water-miscible solvents, such as dextrose, sorbitol, glycerol, propylene glycol, polyethylene glycol, aliphatic alcohols, and the like, and non-water-miscible solvents such as mineral oils, vegetable oils and the like, in which the therapeutic agent may be soluble or suspended by means of a known surfactant agent.

For parenteral administration, the doses may be prepared according to standard processes, which can contain the active principle formulated as the main active ingredient. A wide variety of liquid formulations, such as injectable sterile solutions, utilize inert diluents such as double-distilled water, mineral oils, vegetable oils, propylene glycol, polyethylene glycols 300-400, aliphatic and aromatic alcohols or several other water-miscible or -immiscible solvents in which the therapeutic agent is soluble or may be suspended. For example pharmaceutically acceptable injectable formulation containing 0.039% of active principle designated Subcomposition-3, prepared according to standard processes in sterile water for injections and administered intraperitoneally. For example, pharmaceutically acceptable injectable formulation containing 1% of active principle designated Composition, prepared according to standard processes in sterile water for injections and administered intraperitoneally. Another variety of solid formulations such as sterile powders to be suspended or solubilized in a pharmaceutically acceptable solvent.

For buccal and sublingual administration, the active ingredient may be formulated in the form of tablets with water-soluble binding agents such as lactose and other pleasant-tasting carbohydrates.

For rectal and vaginal administration and other unconventional administrations, the active ingredient may be formulated in the form of a suppository, pessary or insert, suspended in inert agents such as cocoa butter, semisynthetic glycerides, petroleum jellies or other natural lubricants, or synthetic emollients such as polyethylene glycol 1000 or polyethylene glycol 4000.

A number of transdermal formulations of the invention may be used to dispense discrete doses of the active agent at a controlled rate through the skin to produce a systemic effect. One transdermal system comprises an outer cover as barrier, a reservoir matrix of the drug which can contain a controlled-release membrane and a contact adhesive for anchoring the system with a protective layer which should be removed before applying the device to the skin surface. The drug reservoir is normally some type of matrix of polymers such as PVP or a silicone polymer, from which the drug is released slowly. A microporous membrane such as polypropylene film which may serve to control the rate of release.

TOXICOLOGICAL STUDIES

Toxicological studies carried out in the Institute of Public Health of Chile, Department F.A.S.I., comprise the ocular irritation test and the skin toxicity test (modified Draize test).

Ocular Irritation

The ocular irritation consists in instilling 0.1 ml of the sample (0.1 g sample/0.1 ml) in the left eye of each of 6 rabbits weighing 2500 to 3000 grams; the right eye is left as a healthy control. Observation period at 24, 48 and 72 hours, respectively. The reaction is considered positive when any one of the observations reveals discernible opacity in the cornea and/or ulceration of the cornea and/or diffuse irritation of the cornea with reddening and discernible vessels on simple inspection (conjunctivitis) and/or blepharitis. A product is an ocular irritant when 4 of the 6 rabbits display some of these symptoms.

Six eyes of rabbits treated with the sample of the Composition were evaluated with respect to the corresponding control eye at 24, 48 and 72 hours. The result of the test is a harmless product.

Skin Toxicity

Skin toxicity (modified Draize test) is the evaluation of skin reactions of 4 rabbits weighing 2500 to 3000 g. The lesions produced at 24 hours are observed on healthy skin and on scarified skin, evaluating the appearance of erythema, edema and necrosis, considering the intensity of lesion. The product or sample is harmless when no erythema, edema and necrosis are present; it is slightly toxic when erythema and edema are barely perceptible; it is toxic when the lesion of erythema and edema is well defined and highly toxic when the lesion is severe in erythema, edema and necrosis.

Four scarified skins and four healthy skins treated with the sample of the Composition were evaluated at 24 hours. The result of the test does not display erythema, edema or necrosis, the test product designated COMPOSITION being classified as harmless.

Toxicological studies carried out at the University of Chile, Faculty of Chemical and Pharmaceutical Sciences, comprise the $LD_{50}/7$, cytotoxicity/7 and genotoxicity (micronuclei/30 hours) tests.

Acute Toxicity ($LD_{50}/7$)

Study of acute toxicity at a single dose, determination of the median lethal dose at 7 days, for CF1 strain mouse species weighing 30 grams on average, intraperitoneal sample administration route, dose administered 250 mg/kg body weight and 750 mg/kg body weight (maximum administrable dose) of Composition in physiological saline. 20 animals for each treatment (250 mg/kg sample, 750 mg/kg sample, positive control and negative control).

An evaluation was carried out of the behavioral signs over the 7 days allowed for the treatment with the Composition, 0% of mortality being observed for the i.p. doses of both 250 and 750 mg/kg body weight, and no differences are seen with respect to the control group which was subjected to the same experimental conditions using only physiological saline. It is deduced from the results that the test product designated COMPOSITION does not produce mortality at the experimental doses tested.

Acute Cytotoxicity

Study of acute toxicity at a single dose, determination of cytotoxicity at 7 days, for CF1 strain mouse species weighing 30 grams on average, intraperitoneal sample administration route, dose administered 30 mg/kg body weight of Composition in physiological saline. 20 animals for each treatment (sample, positive control and negative control). Macroscopic inspection of target organs: liver, lung, kidney, cardiac muscle, skeletal muscle, thyroid, adrenal glands and spleen, and subsequent histological examination of same.

The evaluation is carried out on the target organs, lung, kidney, cardiac muscle, skeletal muscle, thyroid and adrenal glands proving to display normal histology and macroscopic appearance. Of the mice examined, 95% show white nodules in the liver and spleen. Histological examination reveals a foreign body lesion which only threatens the Glisson's capsule and the *capsula lienis*, respectively, not affecting the parenchyma of these organs, which display normal histology. It is deduced from the results that the test product designated COMPOSITION is not cytotoxic at the experimental doses tested.

Acute Genotoxicity (Micronuclei)

Study of acute toxicity at a single dose, determination of genotoxicity by means of the micronuclei test at 30 hours of treatment, in CF1 strain mouse species weighing 32 grams on average, intraperitoneal administration route, dose administered 500 mg/kg body weight of Composition in physiological saline, 10 animals for each treatment (sample, positive control and negative control).

A count is done of the number of polychromatic erythrocytes with micronucleus (PCEMN) in 1000 polychromatic erythrocytes (PCE), and number of mature erythrocytes (ME) in 300 PCE.

The PCEMN values, expressed as a percentage, fall within the normal baseline limits accepted for micronuclei, no differences being seen with respect to the experimental negative control and the long established negative control of the Toxicological Genetics laboratory at the experimental doses administered. The cell count is representative, since it is deduced from the toxicity rate that the test compound designated COMPOSITION is not cytotoxic for the cell populations evaluated, that is to say PCE and ME.

PRECLINICAL THERAPEUTIC APPLICATIONS OF THE INVENTION

Description of the Preclinical Experiment in Guinea Pigs

The traditional test of greater sensitivity described in the bibliography is the technique of quantitative evaluation of intradermoplantar edema, based on the method, "A modified plethysmographic apparatus for recording volume changes in the rat paw" (Harris J. M. and P. S. J. Spencer, 1962) and adapted using carrageenan in rats by (H. Ohnishi et al., 1981; D. Chu and B. Kovacs, 1977). This technique, modified by the inventor (Fuentes V., 1992) in the present preclinical investigation, develops the study of the biological response induced on inoculating lambda-carrageenan into the plantar pad of guinea pigs. This inoculation initiates an inflammatory process defined as the standard inflammatory constant of all the preclinical trials.

The anti-inflammatory effect of a drug or medicinal product is evaluated clinically by inducing a standardized inflammatory process. Accordingly, it is necessary to use a biological model which evaluates the inflammatory response after the administration of a standardized inflammatory noxa. The design of the preclinical experiment should permit evaluation of the anti-inflammatory process following the application of a known anti-inflammatory drug or medicinal product—anti-inflammatory reference substance—or of an anti-inflammatory composition and/or subcompositions (invention), evaluating the inflammatory results comparatively between noxa, reference substances and samples of the invention.

The anti-inflammatory response of a drug is the result of the interaction of the inflammatory variables of the standard versus the anti-inflammatory variables of the reference substances and samples. The results thereof are analyzed by means of the comparative evaluation of the responses of the samples of drug and pharmaceutical dosage forms applied via different administration routes. The comparative evaluation is performed by measuring with a plethysmometer the change in volume in milliliters of mercury and expressing the results in absolute volume (ml) and relative percentage (°/l or %) values versus the variable of time in hours (h).

Method of Measurement

The study of the anti-inflammatory effectiveness of a drug is carried out using the technique of quantitative evaluation of intradermoplantar edema induced in rat paws (Harris and Spencer, 1962; D. Chu and B. Kovacs, 1977).

The inflammatory response is induced by inoculating carrageenan into the animal's plantar pad, and the change in volume is measured with a plethysmometer in milliliters of mercury. The results are expressed in values of absolute inflamed volume and proportion of relative inflamed volume versus the variable of time in hours (H. Ohnishi et al., 1981).

The technique employed is adapted to a biological model of guinea pigs, and evaluates the intensity of the edema as the increase or decrease in the proportion of relative inflamed volume. The equation which describes this variable is: postinoculation volume minus preinoculation control volume divided by preinoculation control volume.

The method of measurement is composed of three basic steps:

Measurement of the clinical parameter inflammation volume obtained on inoculating an inflammatory noxa. This procedure constitutes the inflammatory standard (inflammatory control).

Measurement of the change in the clinical parameter inflammation volume by applying to the inflammatory standard a drug recognized as anti-inflammatory reference substance (anti-inflammatory control).

Measurement of the change in the clinical parameter inflammation volume by applying to the inflammatory standard an anti-inflammatory composition and/or sub-compositions (invention).

Intraperitoneal Application of the Composition in Animals

Objective: Measurement of the anti-inflammatory effect and lethality of the formulation Sample-5 (M5) which contains the active principle designated COMPOSITION, compared with a control reference anti-inflammatory drug, acetylsalicylic acid (P1), and both compared with a control standard inflammatory agent, lambda-carrageenan (S2), employing male Pirbright strain non-consanguineous guinea pigs between 3 and 5 weeks old and weighing between 250 and 350 grams; number of animals 45 and readings 330.

Methodology: Comparative evaluation of the decrease in intradermoplantar edema in guinea pigs Standard (S2): 0.1 ml of the pharmaceutically acceptable injectable formulation containing 1% of lambda-carrageenan, prepared according to standard processes in sterile water for injections and administered via the intradermoplantar route. Single dose of carrageenan between 3.6 and 3.9 mg/kg animal body weight.

Reference substance (P1): 2.0 ml of the pharmaceutically acceptable injectable formulation containing 6.25% of acetylsalicylic acid (ASA), prepared according to standard processes in sterile water for injections and administered intraperitoneally. Single dose of ASA, between 418.1 and 490.2 mg/kg animal body weight.

Summary of examples of preclinical application of the invention
A summary table of the preclinical therapeutic applications carried out on a biological model using guinea pigs is presented below.

| Description | | Meaing | Inflam. Drug. (sol.) | Anti-inflam. Drug | Pharmaceutical Dosage Form | Anti-inflam. Ad. Rte. | Conc. % | Dose mg/kg animal body wt. |
|---|---|---|---|---|---|---|---|---|
| Inflammatory | S1 | Standard-1 | CARR | — | Solution | i.d.p. | 1.0 | 3.3–4.1 |
| standard | S2 | Standard-2 | CARR | — | Solution | i.d.p. | 1.0 | 3.6–3.9 |
| Anti- | P1 | Reference-1 | CARR | ASA | Solution | i.p. | 6.25 | 418.1–490.2 |
| inflammatory reference | P2 | Reference-2 | CARR | DICLO | Solution | i.p. | 2.50 | 94.8–105.8 |
| Composition | M1 | Sample-1 | CARR | COMP | Solution | i.p. | 5.0 | 172.4–184.5 |
| anti- | M2 | Sample-2 | CARR | COMP | Gel | topical | 1.0 | 45.3–61.5 |
| inflammatory | M3 | Sample-3 | CARR | COMP | Solution | i.p. | 0.1 | 2.2–2.6 |
| samples | M4 | Sample-4 | CARR | COMP | Solution | i.p. | 0.1 | 3.7–5.3 |
| | M5 | Sample-5 | CARR | COMP | Solution | i.p. | 1.0 | 62.5–72.7 |
| Gel | G1 | Gel Sample-1 | CARR | COMP | Gel | topical | 1.0 | 72.2–78.4 |
| Composition | G2 | Gel Sample-2 | CARR | COMP | Gel | topical | 1.0 | 66.9–78.4 |
| anti-inflammatory samples | G3 | Gel Sample-3 | CARR | COMP | Gel | topical | 1.0 | 68.2–75.2 |
| Subcomp. | SC1 | Sample-SC1 | CARR | SUBCOMP1 | Solution | i.p. | 0.023 | 0.8–0.9 |
| anti- | SC2 | Sample-SC2 | CARR | SUBCOMP2 | Solution | i.p. | 0.0183 | 0.6–0.7 |
| inflammatory | SC3 | Sample-SC3 | CARR | SUBCOMP3 | Solution | i.p. | 0.039 | 1.3–1.4 |
| samples | SC4 | Sample-SC4 | CARR | SUBCOMP4 | Solution | i.p. | 0.037 | 1.2–1.4 |

CARR = lambda-carrageenan
ASA = acetylsalicylic acid
DICLO = diclofenac sodium
COMP = Composition
SUBCOMP 1 to 4 = Subcompositions 1 to 4
i.d.p. = intradermoplantar
i.p. = intraperitoneal
topical = topical The examples which follow provide us with a better understanding of the invention without thereby limiting its field of application.

EXAMPLE 11

Comparative systemic evaluation of the anti-inflammatory effect of the composition versus ASA and inflammatory standard.

Sample-5 (M5): 2.0 ml of the pharmaceutically acceptable injectable formulation containing 1% of active principle designated Composition, prepared according to standard processes in sterile water for injections and administered intraperitoneally. Single dose of the Composition, between 62.5 and 72.7 mg/kg animal body weight.

Results
Percentage Inflammation and lethality versus time (hours)

| Time (hours) | % Inflammation Carrageenan (S2) | % Inflammation ASA (P1) | % Inflammation Sample-5 (M5) | % Lethality |
|---|---|---|---|---|
| 0.00 | 00.000 | 00.000 | 00.000 | 0 |
| 1.00 | 09.142 | 05.620 | 03.479 | 0 |
| 2.00 | 22.480 | 13.700 | 05.130 | 0 |
| 3.00 | 23.168 | 10.450 | 04.245 | 0 |
| 4.00 | 52.411 | 12.020 | 06.545 | 0 |
| 5.00 | 57.107 | 12.100 | 05.307 | 0 |
| 6.00 | 18.284 | 10.450 | 04.363 | 0 |
| 7.00 | — | 09.810 | — | 0 |

It is concluded from the analysis of the data that both Sample-5 (M5) and the reference ASA (P1) produce a significant anti-inflammatory effect (p<0.000 according to one way variance analysis and Tukey's multiple comparisons with family error rate=0.01) with respect to the carrageenan standard (S2), at the experimental doses used.

It is concluded that Sample-5 (M5) produces a significantly greater anti-inflammatory effect (p<0.000 according to one way variance analysis and Tukey's multiple comparisons with family error rate=0.01) than ASA, at the experimental doses used.

Sample-5 (M5) in the injectable pharmaceutical dosage form possesses good intraperitoneal (systemic) tolerability with 0% lethality.

EXAMPLE 12

Comparative systemic evaluation of the anti-inflammatory effect of the composition versus diclofenac Na and inflammatory standard.

Intraperitoneal Application of the Composition in Animals

Objective: Measurement of the anti-inflammatory effect and lethality of the formulation Sample-5 (M5) which contains the active principle designated COMPOSITION, compared with a control reference anti-inflammatory drug, diclofenac sodium (P2), and both compared with a control standard inflammatory agent, lambda-carrageenan (S2), employing male Pirbright strain non-consanguineous guinea pigs between 3 and 5 weeks old and weighing between 250 and 350 grams; number of animals 30 and readings 200.

Methodology: Comparative evaluation of the decrease in intradermoplantar edema in guinea pigs Standard (S2): 0.1 ml of the pharmaceutically acceptable injectable formulation containing 1% of lambda-carrageenan, prepared according to standard processes in sterile water for injections and administered via the intradermoplantar route. Single dose of carrageenan between 3.6 and 3.9 mg/kg animal body weight.

Reference substance (P2): 1.1 ml of the pharmaceutically acceptable injectable formulation containing 2.5% of diclofenac sodium, prepared according to standard processes in sterile water for injections, propylene glycol and injectable benzyl alcohol and administered intraperitoneally. Single dose of diclofenac sodium, between 94.8 and 105.8 mg/kg animal body weight.

Sample-5 (M5): 2.0 ml of the pharmaceutically acceptable injectable formulation containing 1% of active principle designated Composition, prepared according to standard processes in sterile water for injections and administered intraperitoneally. Single dose of the Composition, between 62.5 and 72.7 mg/kg animal body weight.

Results
Percentage Inflammation and lethality versus time (hours)

| Time (hours) | % Inflammation Carrageenan (S2) | % Inflammation DICLO (P2) | % Inflammation Sample-5 (M5) | % Lethality |
|---|---|---|---|---|
| 0.00 | 00.000 | 00.000 | 00.000 | 0 |
| 1.00 | 09.142 | 12.500 | 03.479 | 0 |
| 2.00 | 22.480 | 12.600 | 05.130 | 0 |
| 3.00 | 23.168 | 14.300 | 04.245 | 0 |
| 4.00 | 52.411 | 14.500 | 06.545 | 0 |
| 5.00 | 57.107 | 11.400 | 05.307 | 0 |
| 6.00 | 18.284 | 12.300 | 04.363 | 0 |

It is concluded from the analysis of the data that both Sample-5 (M5) and the reference diclofenac sodium (P2) produce a significant anti-inflammatory effect (p<0.000 according to one way variance analysis and Tukey's multiple comparisons with family error rate=0.01) with respect to the carrageenan standard (S2), at the experimental doses used.

It is concluded that Sample-5 (M5) produces a significantly similar anti-inflammatory effect (p<0.000 according to one way variance analysis and Tukey's multiple comparisons with family error rate=0.01) to diclofenac sodium, at the experimental doses used.

Sample-5 (M5) in the injectable pharmaceutical dosage form possesses good intraperitoneal (systemic) tolerability with 0% lethality.

EXAMPLE 13

Comparative topical evaluation of the anti-inflammatory effect of the composition versus ASA and inflammatory standard

Topical Application of the Composition Administered as Gels in Animals

Objective: Measurement of the anti-inflammatory effect and allergic reaction of the formulation Gel Sample-3 (G3) which contains the active principle designated COMPOSITION, compared with a control reference anti-inflammatory drug, ASA (Pi), and both compared with a control standard inflammatory agent, lambda-carrageenan (S2), employing male Pirbright strain non-consanguineous guinea pigs between 3 and 5 weeks old and weighing between 250 and 350 grams; number of animals 45 and readings 330.

Methodology: Comparative evaluation of the decrease in intradermoplantar edema in guinea pigs Standard (S2): 0.1 ml of the pharmaceutically acceptable injectable formulation containing 1% of lambda-carrageenan, prepared according to standard processes in sterile water for injections and administered via the intradermoplantar route. Single dose of carrageenan between 3.6 and 3.9 mg/kg animal body weight.

Reference substance (P1): 2.0 ml of the pharmaceutically acceptable injectable formulation containing 6.25% of acetylsalicylic acid (ASA), prepared according to standard processes in sterile water for injections and administered intraperitoneally. Single dose of ASA, between 418.1 and 490.2 mg/kg animal body weight.

Gel Sample-3 (G3): 2.0 g of the pharmaceutically acceptable gel formulation containing 1% of active principle designated Composition, prepared according to standard processes in a gelling hydrophilic base, such as acrylic acid polymers, humectant and emollient agents such as glycerol, propylene glycol, polyethylene glycol 300-400-1000, preservative agents such as parabens, sterile water for injections, and administered topically. Single dose of the Composition, between 68.2 and 75.2 mg/kg animal body weight.

| | | Results | | |
|---|---|---|---|---|
| | | Percentage Inflammation and allergic reaction versus time (hours) | | |
| Time (hours) | % Inflammation Carrageenan (S2) | % Inflammation ASA (P1) | % Inflammation Gel Sample-3 (G3) | % Allergic Rx |
| 0.00 | 00.000 | 00.000 | 00.000 | 0 |
| 1.00 | 09.142 | 05.620 | 03.479 | 0 |
| 2.00 | 22.480 | 13.700 | 05.130 | 0 |
| 3.00 | 23.168 | 10.450 | 04.245 | 0 |
| 4.00 | 52.411 | 12.020 | 06.545 | 0 |
| 5.00 | 57.107 | 12.100 | 05.307 | 0 |
| 6.00 | 18.284 | 10.450 | 04.363 | 0 |
| 7.00 | — | 09.810 | — | — |

It is concluded from the analysis of the data that both Gel Sample-3 (G3) and the reference ASA (P1) produce a significant anti-inflammatory effect (p<0.000 according to one way variance analysis and Tukey's multiple comparisons with family error rate=0.01) with respect to the carrageenan standard (S2), at the experimental doses used.

It is concluded that Gel Sample-3 (G3) produces a significantly greater anti-inflammatory effect (p<0.000 according to one way variance analysis and Tukey's multiple comparisons with family error rate=0.01) than the ASA (P1) reference substance and the carrageenan standard (S2), at the experimental doses used.

Gel Sample-3 (G3) in the gel pharmaceutical dosage form possesses good dermatological (topical) tolerability with 0% of allergic reactions.

EXAMPLE 14

Comparative systemic evaluation of the anti-inflammatory effect of the subcompositions versus ASA and inflammatory standard.

Intraperitoneal Applications of the First, Second, Third and Fourth Subcompositions in Animals Objective: Measurement of the anti-inflammatory effect and lethality of the formulations Sample-SC1 (SC1), Sample-SC2 (SC2), Sample-SC3 (SC3) and Sample-SC4 (SC4) which contain the active principle SUBCOMPOSITION-1, SUBCOMPOSITION-2, SUBCOMPOSITION-3 and SUBCOMPOSITION-4, respectively, compared with a control reference anti-inflammatory drug, acetylsalicylic acid (P1), and both compared with a control standard inflammatory agent, lambda-carrageenan (S2), employing male Pirbright strain non-consanguineous guinea pigs between 3 and 5 weeks old and weighing between 250 and 350 grams; number of animals 75 and readings 540.

Methodology: Comparative evaluation of the decrease in intradermoplantar edema in guinea pigs Standard (S2): 0.1 ml of the pharmaceutically acceptable injectable formulation containing 1% of lambda-carrageenan, prepared according to standard processes in sterile water for injections and administered via the intradermoplantar route. Single dose of carrageenan between 3.6 and 3.9 mg/kg animal body weight.

Reference substance (P1): 2.0 ml of the pharmaceutically acceptable injectable formulation containing 6.25% of acetylsalicylic acid (ASA), prepared according to standard processes in sterile water for injections and administered intraperitoneally. Single dose of ASA, between 418.1 and 490.2 mg/kg animal body weight.

Sample-SC1 (SC1): 1.0 ml of the pharmaceutically acceptable injectable formulation containing 0.023% of active principle designated Subcomposition-1, prepared according to standard processes in sterile water for injections and administered intraperitoneally. Single dose of Subcomposition-1, between 0.8 and 0.9 mg/kg animal body weight.

Sample-SC2 (SC2): 1.0 ml of the pharmaceutically acceptable injectable formulation containing 0.0183% of active principle designated Subcomposition-2, prepared according to standard processes in sterile water for injections and administered intraperitoneally. Single dose of Subcomposition-2, between 0.6 and 0.7 mg/kg animal body weight.

Sample-SC3 (SC3): 1.0 ml of the pharmaceutically acceptable injectable formulation containing 0.039% of active principle designated Subcomposition-3, prepared according to standard processes in sterile water for injections and administered intraperitoneally. Single dose of Subcomposition-3, between 1.3 and 1.4 mg/kg animal body weight.

Sample-SC4 (SC4): 1.0 ml of the pharmaceutically acceptable injectable formulation containing 0.037% of active principle designated Subcomposition-4, prepared according to standard processes in sterile water for injections and administered intraperitoneally. Single dose of Subcomposition-4, between 1.2 and 1.4 mg/kg animal body weight.

| | | Results | | | | |
|---|---|---|---|---|---|---|
| | | Percentage Inflammation and lethality versus time (hours) | | | | |
| Time (hours) | % Inflammation Carrageenan (S2) | % Inflammation ASA (P1) | % Inflammation Samples | | | | % Lethality |
| | | | (SC1) | (SC2) | (SC3) | (SC4) | |
| 0.00 | 00.000 | 00.000 | 00.000 | 00.000 | 00.000 | 00.000 | 0 |
| 1.00 | 09.142 | 05.620 | 03.400 | 02.000 | −08.447 | −05.300 | 0 |
| 2.00 | 22.480 | 13.700 | 02.290 | −05.270 | −18.859 | −04.640 | 0 |
| 3.00 | 23.168 | 10.450 | 04.120 | 05.240 | −09.739 | −00.620 | 0 |
| 4.00 | 52.411 | 12.020 | 00.700 | −01.400 | −08.440 | −01.400 | 0 |
| 5.00 | 57.107 | 12.100 | 02.990 | −03.430 | −05.349 | 03.900 | 0 |

-continued

Results
Percentage Inflammation and lethality versus time (hours)

| Time (hours) | % Inflammation Carrageenan (S2) | % Inflammation ASA (P1) | % Inflammation Samples | | | | % Lethality |
| --- | --- | --- | --- | --- | --- | --- | --- |
| | | | (SC1) | (SC2) | (SC3) | (SC4) | |
| 6.00 | 18.284 | 10.450 | 06.540 | −05.850 | −03.625 | −06.990 | 0 |
| 7.00 | — | 09.810 | — | — | — | — | — |

It is concluded from the analysis of the data that both Sample-SC1 (SC1), Sample-SC2 (SC2), Sample-SC3 (SC3) and Sample-SC4 (SC4) and the reference ASA (P1) produce a significant anti-inflammatory effect ($p<0.000$ according to one way variance analysis and Tukey's multiple comparisons with family error rate=0.01) with respect to the carrageenan standard (S2), at the experimental doses used.

It is concluded that Sample-SC1 (SC1), Sample-SC2 (SC2), Sample-SC3 (SC3) and Sample-SC4 (SC4) produce a significantly greater anti-inflammatory effect ($p<0.000$ according to one way variance analysis and Tukey's multiple comparisons with family error rate=0.01) than ASA, at the experimental doses used.

Sample-SC1 (SC1), Sample-SC2 (SC2), Sample-SC3 (SC3) and Sample-SC4 (SC4) in the injectable pharmaceutical dosage form possess good intraperitoneal (systemic) tolerability with 0% lethality.

CLINICAL THERAPEUTIC APPLICATIONS OF THE INVENTION

Description of the Clinical Experiment in Horses

The clinical measurement used in Phase I for evaluating the anti-inflammatory effect qualitatively in horses is based on an indirect technique for the clinical parameter of pain, which evaluates the treatment conditions by means of an algorithm.

The examples which follow provide us with a better understanding of the invention without thereby limiting its field of application.

EXAMPLE 15

Comparative Topical Evaluation of the Anti-inflammatory Effect

Topical Application of the Composition Administered as Gel in Animals, Phase I

Objective: Qualitative clinical evaluation of the anti-inflammatory effect and allergic reaction of the formulation Gel Sample-4 (G4) which contains the active principle designated COMPOSITION, over time, employing male TB racehorses between 5 and 10 years old, weighing between 400 and 550 kilograms, with a diagnosis of traumatic tendinitis in the fetlocks of the fore- and hindlegs; number of animals 4, readings 28.

Methodology: Qualitative comparative evaluation of the decrease in the edema in the fetlocks of the extremities (fore- and hindlegs) in horses.

Gel Sample-4 (G4): 10.0 g of the pharmaceutically acceptable gel formulation containing 5% of active principle designated Composition, prepared according to standard processes in a gelling hydrophilic base, such as acrylic acid polymers, carboxyvinyl resins, humectant and emollient agents such as glycerol, propylene glycol, polyethylene glycol 300-400-1000, preservative agents such as benzoates, parabens, sterile water for injections, and administered topically. Repeated doses of the Composition, between 0.90 and 1.25 mg/kg animal body weight, every 4 hours for 7 days.

From the qualitative veterinary clinical analysis, it is included that Sample Gel-4 (G4) produces a substantive anti-inflammatory effect at the doses used; no topical allergic reaction is observed.

The dose recommended for Phase II (quantitative study) is 1.0 mg/kg body weight every 4 hours.

CLINICAL THERAPEUTIC APPLICATIONS OF THE INVENTION IN HUMANS
Summary of examples of clinical application of the invention

| CLINICAL STUDIES | THERAPEUTIC EFFECT | Administration | Sample Active Substance | Reference Active Substance | Pharm. Form | Dose tested (mg/kg body wt.) |
| --- | --- | --- | --- | --- | --- | --- |
| PHASE I | Analgesic anti-inflammatory | topical | COMPOSITION | — | Gel | 0.1–0.3 |
| | inflammatory | topical | COMPOSITION | — | Gel | 0.3–0.9 |
| | Antipruritic | topical | COMPOSITION | — | Gel | 0.3–0.9 |
| | Antipyretic | oral | COMPOSITION | — | Tabl. | 1.4–2.8 |
| PHASE II | Anti- | oral | COMPOSITION | — | Tabl. | 1.4–2.8 |
| | inflammatory | topical | COMPOSITION | — | Gel | 0.3–0.9–2.7 |
| PHASE III | Analgesic | topical | COMPOSITION | — | Gel | 0.3 |
| | Analgesic anti-inflammatory Analgesic anti-inflammatory Analgesic anti-inflammatory | topical | — | ETOFENAMATE | Gel | 1.5 |

EXAMPLE 16

Topical Anti-inflammatory and Analgesic Clinical Evaluation, Phase I.

Topical Application of the Composition, Administered as Gel in Human Beings

Objective: Qualitative evaluation of the anti-inflammatory and analgesic effect and allergic reaction (tolerability) of the formulation Gel Sample-3 (G3) which contains the active principle designated COMPOSITION, in human beings with associated pathologies and without collateral treatments, in increasing prospective doses. Single-blind clinical trial with informed consent.

Patients: 3 female and 1 male, age 35 to 58 years.

Diagnosis: post-traumatic lesion with edema, hematoma, sprain and pain in ankle and/or knee and/or head.

Clinical parameter: inflammation, algesia (pain) and local allergic reaction.

Gel Sample-3 (G3): 0.7 and 2.1 g of the pharmaceutically acceptable gel formulation containing 1% of active principle designated Composition, prepared according to standard processes in a gelling hydrophilic base, such as acrylic acid polymers, humectant and emollient agents such as glycerol, propylene glycol, polyethylene glycol 300-400-1000, preservative agents such as parabens, sterile water for injections, and administered topically.

Dosage: Increasing prospective doses of the Composition, between 0.1 and 0.3 mg/kg patient's body weight, every 4 hours. Minimum 2 applications at 0.1 mg/kg body weight; other subsequent applications at 0.3 mg/kg body weight.

| Results | | |
|---|---|---|
| Dose of the Composition, 0.1 mg/kg body weight | subsidence of inflammation | negative |
| | analgesia | negative |
| | allergic reaction | negative |
| Dose of the Composition, 0.3 mg/kg body weight | subsidence of inflammation | positive |
| | analgesia | positive |
| | allergic reaction | negative |

Conclusions

It is concluded from the analysis of the results that Gel Sample-3 (G3) at a dose in the Composition of 0.3 mg/kg body weight every 4 hours produces a substantive anti-inflammatory and analgesic effect, this being the dose and dosage recommended for the Phase II clinical trial.

It is concluded from the analysis of the results that Gel Sample-3 (G3) at doses in the Composition of 0.1 and 0.3 mg/kg body weight every 4 hours does not produce a topical allergic reaction, displaying good dermatological tolerability.

EXAMPLE 17

Topical Anti-inflammatory and Analgesic Clinical Evaluation, Phase II

Topical Application of the Composition, Administered as Gel in Human Beings

Objective: Qualitative evaluation of the anti-inflammatory and analgesic effect and allergic reaction (tolerability) of the formulation Gel Sample-3 (G3) which contains the active principle designated COMPOSITION, in human beings with associated pathologies and without collateral treatments, in increasing prospective doses. Single-blind clinical trial with informed consent.

Patients: 11 female and 9 male, age 31 to 81 years.

Diagnosis: post-traumatic, rheumatic, idiopathic lesions, postphlebitic syndrome with edema and/or hematoma and/or sprain and/or pain, located in ankle and/or knee and/or shoulder and/or arm and/or elbow and/or hand and/or fingers and/or spine and/or face and/or thigh and/or leg and/or anorectal region.

Clinical parameter: inflammation, algesia (pain) and local allergic reaction.

Gel Sample-3 (G3): 2.1, 6.3 and 18.9 g of the pharmaceutically acceptable gel formulation containing 1% of active principle designated Composition, prepared according to standard processes in a gelling hydrophilic base, such as acrylic acid polymers, humectant and emollient agents such as glycerol, propylene glycol, polyethylene glycol 300-400-1000, preservative agents such as parabens, sterile water for injections, and administered topically.

Dosage: Increasing prospective doses of the Composition, at 0.3, 0.9 and 2.7 mg/kg patient's body weight, every 4 hours. Minimum 2 applications at 0.1 mg/kg body weight; other subsequent applications at 0.3 mg/kg body weight.

| Results | | |
|---|---|---|
| Dose of the Composition, 0.3 mg/kg body weight | subsidence of inflammation | positive |
| | analgesia | positive |
| | allergic reaction | negative |
| Dose of the Composition, 0.9 mg/kg body weight | subsidence of inflammation | positive |
| | analgesia | positive |
| | allergic reaction | negative |
| Dose of the Composition, 2.7 mg/kg body weight | subsidence of inflammation | positive |
| | analgesia | positive |
| | allergic reaction | negative |

Conclusions

It is concluded from the analysis of the results that Gel Sample-3 (G3) at doses in the Composition of 0.3, 0.9 and 2.7 mg/kg body weight every 4 hours produces a substantive anti-inflammatory and analgesic effect, this therapeutic dosage range being recommended for the Phase III clinical trial.

It is concluded from the analysis of the results that Gel Sample-3 (G3) at doses in the Composition of 0.3, 0.9 and 2.7 mg/kg body weight every 4 hours does not produce a topical allergic reaction, displaying good dermatological tolerability.

EXAMPLE 18

Comparative Topical Anti-inflammatory and Analgesic Clinical Evaluation of the Composition Versus Etofenamate, Phase III Topical Application of the Composition, Administered as Gel in Human Beings Objective: Quantitative evaluation of the anti-inflammatory and analgesic effect and allergic reaction (tolerability) of the formulation Gel Sample-3 (G3) which contains the active principle designated COMPOSITION, compared with a control reference anti-inflammatory and analgesic drug, etofenamate gel 5% (P3), in human beings with associated pathologies and without collateral treatments, in repeated doses. Double-blind clinical trial with informed consent, and clinical monitoring with general examination, pressure, blood biochemical profile, Doppler plethysmography and photoplethysmography of the extremities.

Patients: n=34, 30 female and 4 male, age between 24 and 85 years with a mean of 65.3 years.

Diagnosis: traumatic lesions, fractures, postphlebitic syndrome, communicating veins and incompetent veins, with edema, hematoma, sprain, dermatocellulitis, varicophlebitis and bursitis in ankles and/or legs and/or thighs and/or knees and/or wrists and/or hands.

Treatment: ambulatory patient without prior treatment, with home rest and elastic bandage worn continuously, clinical control on days 0, 2, 4, 7, 10 and 15. 18 patients treated with the formulation Sample Gel-3 (G3) and 16 patients with the control reference formulation (P3).

Inflammatory parameters: measurement of perimeter, area and volume of the inflamed region.

Pain parameters: measurement of algesia by means of pain algorithm referred to a universal clinical scale according to: spontaneous pain high, spontaneous pain low, pain with movement high, pain with movement low, provoked pain high, provoked pain low, almost pain-free and pain-free.

Tolerance parameters: local allergic reaction.

Gel Sample-3 (G3): 2.1 g of the pharmaceutically acceptable gel formulation containing 1% of active principle designated Composition, prepared according to standard processes in a gelling hydrophilic base, such as acrylic acid polymers, humectant and emollient agents such as glycerol, propylene glycol, polyethylene glycol 300-400-1000, preservative agents such as parabens, sterile water for injections, and administered topically.

Gel Sample-3 dosage: Repeated doses of the Composition at 0.3 mg/kg patient's body weight, every 4 hours until complete remission with a maximum of 15 days.

Control reference substance (P3): 2.1 g of the pharamecutically acceptable gel formulation containing 5% of active principle designated etofenamate, from an international commercial product registered with the Institute of Public Health of Chile and available on the national ethical market.

Control reference substance (P3) dosage: Repeated doses of etofenamate of 1.5 mg/kg patient's body weight, every 4 hours until complete remission with a maximum of 15 days.

Conclusions

The study of the main objective, the desired hypothesis, is to determine with at least 95% confidence which of the gels, Gel Sample-3 (G3) versus control reference substance (P3), causes inflammation to subside more effectively. It is concluded on the basis of the statistical results that, if the clinical protocol were repeated with the parameters defined, the anti-inflammatory effect of the invention Sample Gel-3 (G3), expressed as a function of the perimeter, area and volume, is significantly greater (p<0.063), (p<0.054) and (p<0.046), respectively, than the anti-inflammatory effect of the control reference medicinal product (P3).

The study of the main objective, the desired hypothesis, is to determine with at least 95% confidence which of the gels, Sample Gel-3 (G3) versus control reference substance (P3), decreases pain more effectively. It is concluded on the basis of the statistical results that, if the clinical protocol were repeated with the parameters defined, the analgesic effect of the invention Gel Sample-3 (G3), expressed as a function of the pain algorithm, is significantly greater (p<0.078) than the analgesic effect of the control reference medicinal product (P3), respectively.

It is concluded from the analysis of the results that Gel Sample-3 (G3) at doses in the Composition of 0.3 mg/kg body weight every 4 hours does not produce a topical allergic reaction, displaying good dermatological tolerability.

EXAMPLE 19

Topical Antipruritic Clinical Evaluation, Phase I

Topical Application of the Composition, Administered as Gel in Human Beings

Objective: Qualitative evaluation of the antipruritic effect and allergic reaction (tolerability) of the formulation Gel Sample-3 (G3) which contains the active principle designated COMPOSITION, in human beings with associated pathologies and without collateral treatments, in repeated doses. Single-blind clinical trial with informed consent.

Patients: 2 female and 3 male, age 2 to 10 years.

Diagnosis: skin, scalp and mucosal lesions caused by varicella zoster, with manifestations of rashes, papules and vesicles.

Clinical parameter: pruritus, itching and local allergic reaction.

Gel Sample-3 (G3): 2.1 and 6.3 g of the pharmaceutically acceptable gel formulation containing 1% of active principle designated Composition, prepared according to standard processes in a gelling hydrophilic base, such as acrylic acid polymers, humectant and emollient agents such as glycerol, propylene glycol, polyethylene glycol 300-400-1000, preservative agents such as parabens, sterile water for injections, and administered topically.

Dosage: Repeated doses of the Composition, at 0.3 and 0.9 mg/kg patient's body weight, every 4 hours.

| Results | | |
|---|---|---|
| Dose of the Composition, 0.3 mg/kg body weight | antipruritic | positive |
| | allergic reaction | negative |
| Dose of the Composition, 0.9 mg/kg body weight | antipruritic | positive |
| | allergic reaction | negative |

Conclusions

It is concluded from the analysis of the results that Gel Sample-3 (G3) at doses in the Composition of 0.3 and 0.9 mg/kg body weight every 4 hours produces a substantive antipruritic effect, this being the dose and dosage recommended for the Phase II clinical trial.

It is concluded from the analysis of the results that Gel Sample-3 (G3) at doses in the Composition of 0.3 and 0.9 mg/kg body weight every 4 hours does not produce a topical allergic reaction, displaying good dermatological tolerability.

EXAMPLE 20

Topical Local Antipyretic Clinical Evaluation, Phase I

Topical Application of the Composition, Administered as Gel in Human Beings

Objective: Qualitative evaluation of the local antipyretic effect and allergic reaction (tolerability) of the formulation Gel Sample-3 (G3) which contains the active principle designated COMPOSITION, in human beings with associated pathologies and without collateral treatments, in repeated doses. Single-blind clinical trial with informed consent.

Patients: 5 female, age 35 to 52 years.

Diagnosis: post-traumatic lesions on knees with edema, hematomas and local hyperthermia.

Clinical parameter: local erythema caloricum, local temperature and local allergic reaction.

Gel Sample-3 (G3): 2.1 and 6.3 g of the pharmaceutically acceptable gel formulation containing 1% of active principle designated Composition, prepared according to standard processes in a gelling hydrophilic base, such as acrylic acid polymers, humectant and emollient agents such as glycerol, propylene glycol, polyethylene glycol 300-400-1000, preservative agents such as parabens, sterile water for injections, and administered topically.

Dosage: Repeated doses of the Composition, at 0.3 and 0.9 mg/kg patient's body weight, every 4 hours.

| Results | | |
| --- | --- | --- |
| Dose of the Composition, 0.3 mg/kg body weight | local antipyretic | positive |
| | allergic reaction | negative |
| Dose of the Composition, 0.9 mg/kg body weight | local antipyretic | positive |
| | allergic reaction | negative |

Conclusions

It is concluded from the analysis of the results that Gel Sample-3 (G3) at doses in the Composition of 0.3 and 0.9 mg/kg body weight every 4 hours produces a substantive local antipyretic effect, this being the dose and dosage recommended for the Phase II clinical trial.

EXAMPLE 21

Enteric Systemic Anti-inflammatory Clinical Evaluation, Phase I

Enteric Application of the Composition, Administered as a Tablet in Human Beings Objective: Qualitative evaluation of the anti-inflammatory effect and allergic reaction (tolerability) of the formulation Com Sample-1 (C1) which contains the active principle designated COMPOSITION, in human beings with associated pathologies and without collateral treatments, in increasing prospective doses. Single-blind clinical trial with informed consent.

Patients: 1 female, age 46 years.

Diagnosis: postoperative (20 days) unilateral diffuse idiopathic intramammary edema in left breast.

Clinical parameter: inflammation and allergic reaction.

Com Sample-1 (C1): uncoated tablet, formulated by a pharmaceutically acceptable dry method, containing 100 mg of active principle designated Composition, prepared according to standard processes in an inert diluent, for example microcrystalline cellulose, ditab, dipac, direct-tableting lactose, lubricants, antiadhesive agents and glidants such as talc, magnesium stearate, polyethylene glycol 6000, and administered orally.

Dosage: Increasing prospective doses of the Composition, between 100 and 200 mg, equivalent to 1.4 and 2.8 mg/kg patient's body weight, every 8 hours.

| Results | | |
| --- | --- | --- |
| Dose of the Composition, 100 mg | subsidence of inflammation | positive |
| | allergic reaction | negative |
| Dose of the Composition, 200 mg | subsidence of inflammation | positive |
| | allergic reaction | negative |

Conclusions

It is concluded from the analysis of the results that Com Sample-I (C1) at doses in the Composition of 100 and 200 mg, equivalent to 1.4 and 2.8 mg/kg body weight, every 8 hours produces a substantive anti-inflammatory and analgesic effect, this being the dose and dosage recommended for the Phase II clinical trial.

It is concluded from the analysis of the results that Com Sample-1 (C1) at doses in the Composition of 100 and 200 mg, equivalent to 1.4 and 2.8 mg/kg body weight, every 8 hours does not produce an allergic reaction, displaying good enteric and/or systemic tolerability.

EXAMPLE 22

Enteric Systemic Analgesic Clinical Evaluation, Phase I

Enteric Application of the Composition, Administered as a Tablet in Human Beings Objective: Qualitative evaluation of the analgesic effect and allergic reaction (tolerability) of the formulation Com Sample-I (C1) which contains the active principle designated COMPOSITION, in human beings with associated pathologies and without collateral treatments, in increasing prospective doses. Single-blind clinical trial with informed consent.

Patients: 2 female and 2 male, age between 35 and 37 years.

Diagnosis: idiopathic headache.

Clinical parameter: algesia (pain) and allergic reaction.

Com Sample-1 (C1): uncoated tablet, formulated by a pharmaceutically acceptable dry method, containing 100 mg of active principle designated Composition, prepared according to standard processes in an inert diluent, for example microcrystalline cellulose, ditab, dipac, direct-tableting lactose, lubricants, antiadhesive agents and glidants such as talc, magnesium stearate, polyethylene glycol 6000, and administered orally.

Dosage: Increasing prospective doses of the Composition, between 100 and 200 mg, equivalent to 1.4 and 2.8 mg/kg patient's body weight, every 8 hours.

| Dose of the Composition, 100 mg | analgesia | positive |
| --- | --- | --- |
| | allergic reaction | negative |
| Dose of the Composition, 200 mg | analgesia | positive |
| | allergic reaction | negative |

Conclusions

It is concluded from the analysis of the results that Com Sample-i (C1) at doses in the Composition of 100 and 200 mg, equivalent to 1.4 and 2.8 mg/kg body weight, every 4 hours produces a substantive analgesic effect, this being the dose and dosage recommended for the Phase II clinical trial.

It is concluded from the analysis of the results that Com Sample-I (C1) at doses in the Composition of 100 and 200 mg. equivalent to 1.4 and 2.8 mg/kg body weight, every 4 hours does not produce an allergic reaction, displaying good enteric and/or systemic tolerability.

BIBLIOGRAPHY

American Society of Hospital Pharmacists.: "Drug Information 1995", thirty-sixth edition, published by the American Society of Hospital Pharmacists Inc., USA, 1995.

Canadian Council on Animal Care.: "Guide to the Care and Use of Experimental Animals Vol. 1", 2nd edition, Canadian Council on Animal Care, Ottawa, 1980.

Corning Incorporated Science Products Division.: "Corning Glassware Catalog 94–95", USA, 1994.

Chu D., and Kovacs B. A.: "Anti-Inflammatory Activity in Oak Gall Extracts", Arch. Int. Pharmacodyn., 230, 166–176, (1977).

Dawson B. and Trapp R.: "Biosestadística Médica" [Medical Biostatistics], 1st edition, published by El Manual Moderno S.A. de C.V., Mexico, 1993.

Fitz-Gibbon C., and Morris L.: "How to Analyze Data", 2nd edition, published by SAGE Publications Inc., University of California, USA, 1987.

Flórez J., Armijo J. A., Mediavilla A.: "Farmacología Humana" [Human Pharmacology], 2nd edition, Ediciones Científicas y Técnicas Masson-Salvat Medicina, Spain, 1992.

Goodman and Gilman.: "Las Bases Farmacológicas de la Terapéutica" [The Pharmacological Bases of Therapy], 5th edition, published by Médica Panamericana, Buenos Aires, 1991.

Harris, J. M. and Spencer, P. S. J.: "A modified plethysmographic apparatus for recording volume changes in the rat paw". J. Pharm. Pharmacol, 14, 464–466, (1962).

Hodgson J.: "Carbohydrate Based Therapeutics", Bio/Technology, 9, 609–613, (1991).

Ohnishi H. et al.: "Anti-inflammatory Properties of newly synthesized compounds, 6-chloro-4-oxyimino-1-phenyl-1,2,3,4-tetrahydroquinoline (M-7074)", Japan J. Pharmacol., 31, 747–756, (1981).

Rang H. P. and Dale M. M.: "Farmacología" [Pharmacology], 2nd edition, Alhambra Longman, S. A., Spain, 1992.

Sharon N. and Lis H.: "Carbohidratos en el Reconocimiento Celular" [Carbohydrates in Cell Recognition], Investigación y Ciencia, March, 20–27 (1993).

Velo G. P. et al.: "La Inflamación, Compendio de Trabajos" [Inflammation, Compendium of Work], 1980.

We claim:

1. A composition derived from a plant of the Cactaceae family, said composition consists essentially of a mixture of:

a) an aromatic amine of formula $C_8H_{11}O_2N$, selected from:

1-R-hydroxy-1-(-4-hydroxy-phenyl-)-2-amino-ethane
   1-S-hydroxy-1-(-4-hydroxy-phenyl-)-2-amino-ethane with molecular structures:

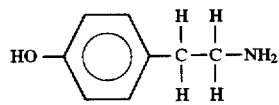

1-S-hydroxy-1-(-4-hydroxy-phenyl-)-2-amino-ethane

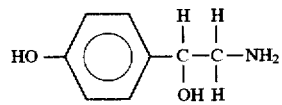

1-R-hydroxy-1-(-4-hydroxy-phenyl-)-2-amino-ethane respectively;

b) a disaccharide of formula $C_{10}H_{18}O_9$; selected from:
   n1-O-($\alpha,\beta$)-(D, L)-ribofuranosyl-($\alpha,\beta$)-(D,L)-ribofuranose;
   Where: n1=carbon 1, 2, 3, 5;
   with molecular structures:

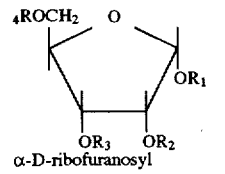
α-D-ribofuranosyl

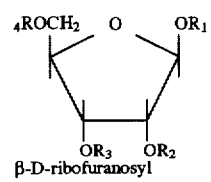
β-D-ribofuranosyl

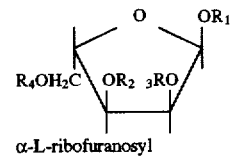
α-L-ribofuranosyl

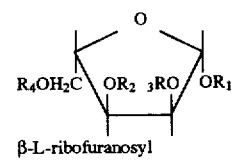
β-L-ribofuranosyl respectively, wherein, when any one of R1, R2, R3 and R4, in the respective, α-D-ribofuranosyl, α-D-ribofuranosyl, α-L-ribofuranosyl, β-L-ribofuranosyl, is selected from:

1-O-α-D-RIBOFURANOSE;
2-O-α-D-RIBOFURANOSE;
3-O-α-D-RIBOFURANOSE;
5-O-α-D-RIBOFURANOSE;
1-O-β-D-RIBOFURANOSE;
2-O-β-D-RIBOFURANOSE;
3-O-β-D-RIBOFURANOSE;
5-O-β-D-RIBOFURANOSE;
1-O-α-L-RIBOFURANOSE;
2-O-α-L-RIBOFURANOSE;
3-O-α-L-RIBOFURANOSE;
5-O-α-L-RIBOFURANOSE;
1-O-β-L-RIBOFURANOSE;
2-O-β-L-RIBOFURANOSE;
3-O-β-L-RIBOFURANOSE;
5-O-β-L-RIBOFURANOSE;

the remaining R1, R2, R3 and R4 are each H, respectively, in the α-D-ribofuranosyl, β-D-ribofuranosyl, α-L-ribofuranosyl, β-L-ribofuranosyl, respectively; and c) one or more structural isomers of the monosaccharides of:

i) galactose, with formula $C_6H_{12}O_6$; selected from: D-galactose; α-D-galactopyranose; β-D-galactopyranose; α-D-galactofuranose; β-D-galactofuranose; L-galactose; α-L-galactopyranose; β-L-galactopyranose; α-L-galactofuranose; β-L-galactofuranose
with molecular structures:

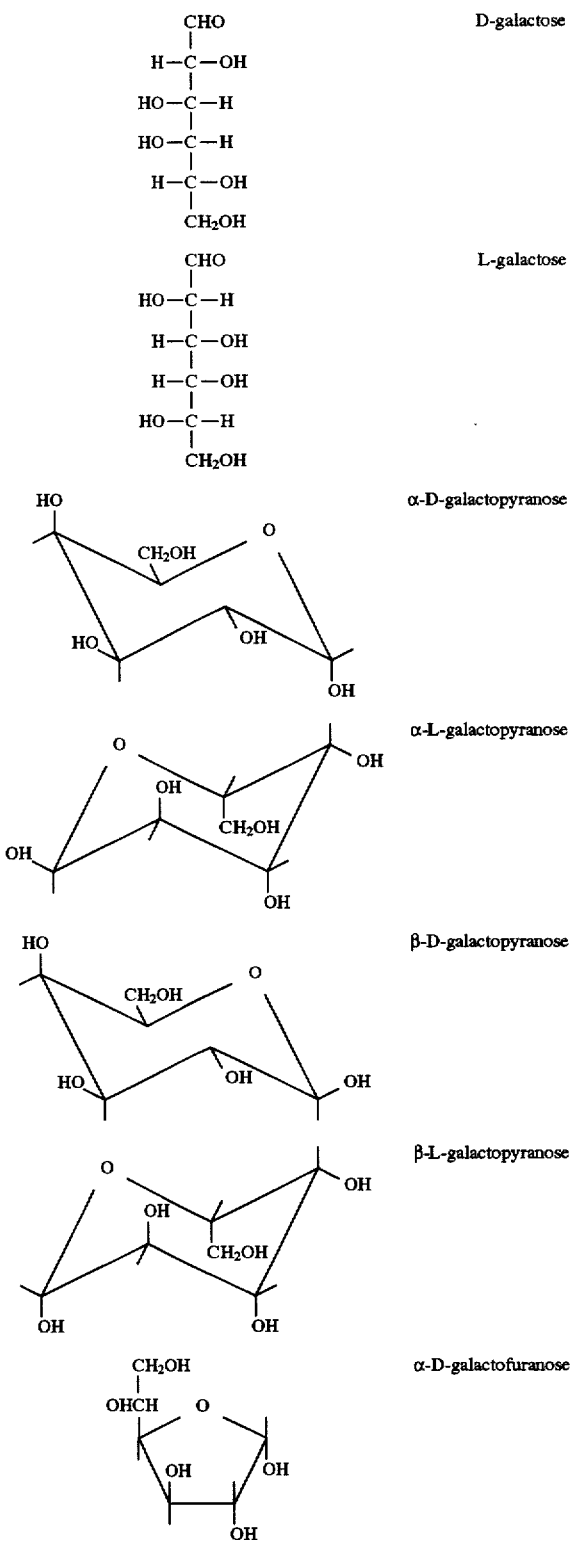

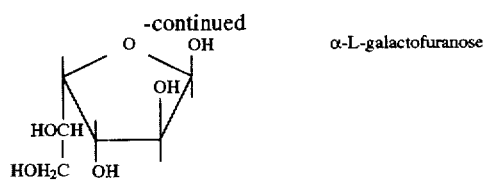

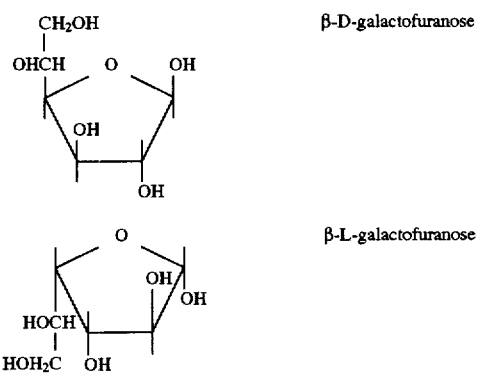

respectively;

ii) mannose with formula $C_6H_{12}O_6$; selected from: D-mannose; α-D-mannopyranose; β-D-mannopyranose; α-D-mannofuranose; β-D-mannofuranose; L-mannose; α-L-mannopyranose; β-L-mannopyranose; α-L-mannofuranose; β-L-mannofuranose
with molecular structures:

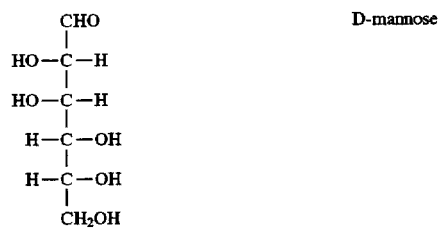

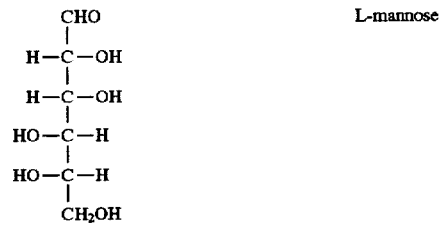

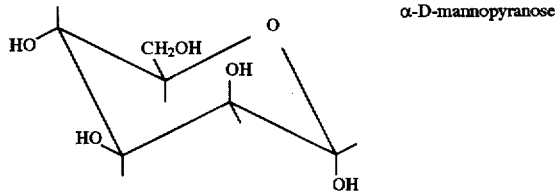

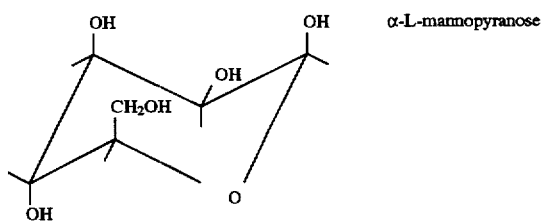

-continued

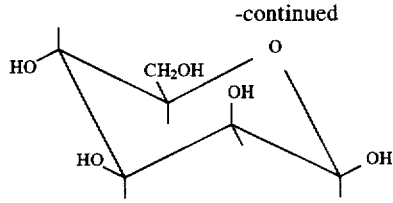 β-D-mannopyranose

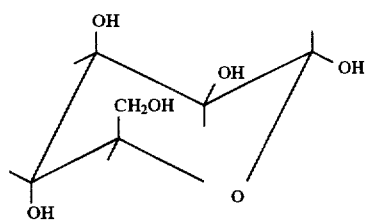 β-L-mannopyranose

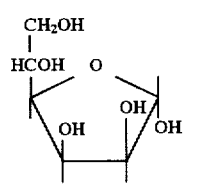 α-D-mannofuranose

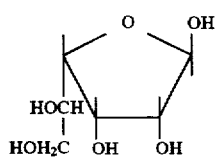 α-L-mannofuranose

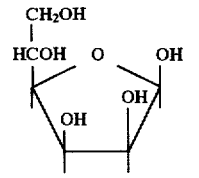 β-D-mannofuranose

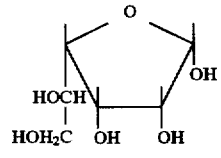 β-L-mannofuranose respectively iii) ribose with formula $C_5H_{10}O_5$; selected from:
D-ribose; α-D-ribofuranose; β-D-ribofuranose
L-ribose; α-L-ribofuranose; β-L-ribofuranose
with molecular structures:

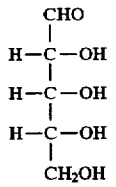 D-ribose

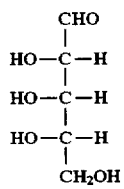 L-ribose

-continued

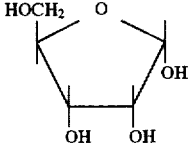 α-D-ribofuranose

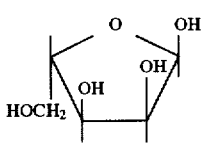 α-L-ribofuranose

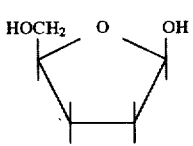 β-D-ribofuranose

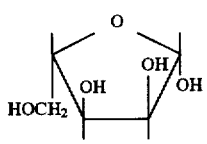 β-L-ribofuranose respectively;

iv) glucose with formula $C_6H_{12}O_6$; selected from:

D-glucose; α-D-glucopyranose; β-D-glucopyranose; α-D-glucofuranose; β-D-glucofuranose L-glucose; α-L-glucopyranose; β-L-glucopyranose; α-L-glucofuranose; β-L-glucofuranose with molecular structures:

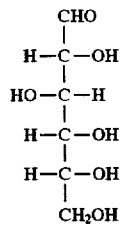 D-glucose

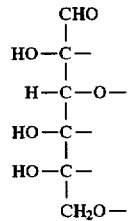 L-glucose

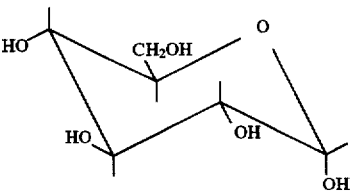 α-D-glucopyranose

-continued

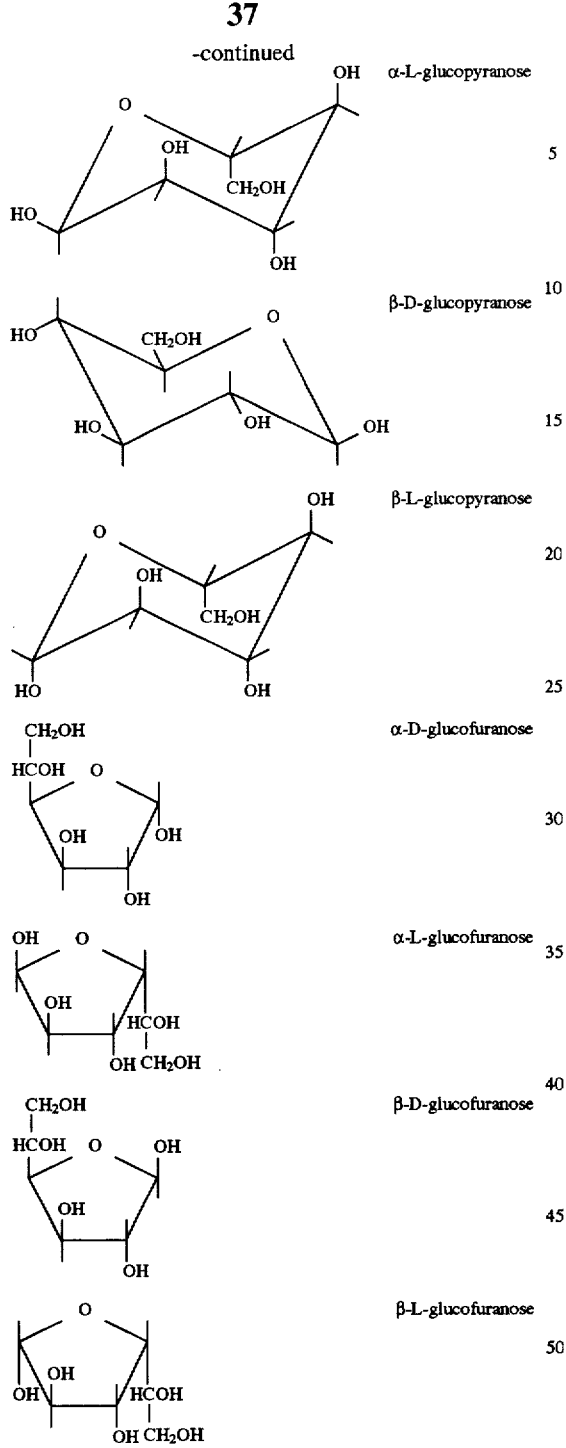

α-L-glucopyranose

β-D-glucopyranose

β-L-glucopyranose

α-D-glucofuranose

α-L-glucofuranose

β-D-glucofuranose

β-L-glucofuranose respectively;

v) fucose with formula $C_6H_{12}O_5$; selected from:
D-fucose, δ6-deoxy-D-galactose; α-D-fucopyranose, δ6-deoxy-α-D-galactopyranose; β-D-fucopyranose, δ6-deoxy-β-D-galactopyranose; α-D-fucofuranose, δ6-deoxy-α-D-galactofuranose; β-D-fucofuranose, δ6-deoxy-β-D-galactofuranose L-fucose, δ6-deoxy-L-galactose; α-L-fucopyranose, δ6-deoxy-α-L-galactopyranose; β-L-fucopyranose, δ6-deoxy-β-L-galactopyranose; α-L-fucofuranose, δ6-deoxy-α-L-galactofuranose; β-L-fucofuranose, δ6-deoxy-β-L-galactofuranose;

with molecular structures:

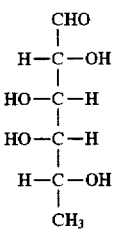

D-fucose, σ 6-deoxy-D-galactose

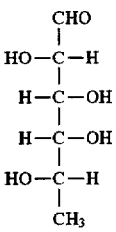

L-fucose σ 6-deoxy-L-galactose

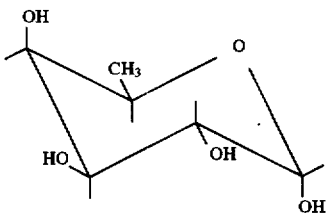

α-D-fucopyranose, σ 6-deoxy-α-D-galactopyranose

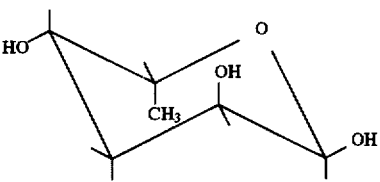

α-L-fucopyranose, σ 6-deoxy-α-L-galactopyranose

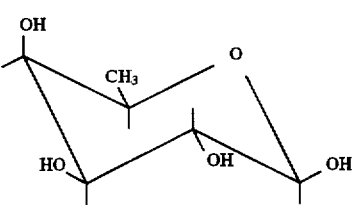

β-D-fucopyranose, σ 6-deoxy-β-D-galactopyranose

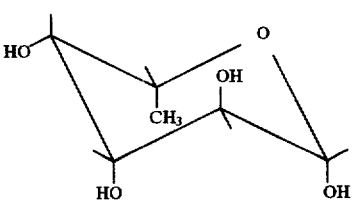

β-L-fucopyranose, σ 6-deoxy-β-L-galactopyranose

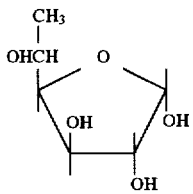

α-D-fucofuranose, σ 6-deoxy-α-D-galactofuranose

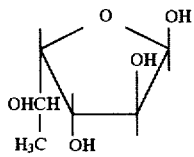

α-L-fucofuranose, σ 6-deoxy-α-L-galactofuranose

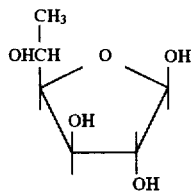

β-D-fucofuranose, σ 6-deoxy-β-D-galactofuranose

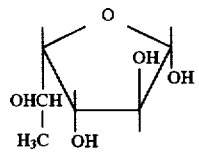

β-L-fucofuranose, σ 6-deoxy-β-L-galactofuranose respectively;
wherein said monosaccharides are in any one of:
- (1) a pyranoside ring form,
- (2) a furanoside ring form, and
- (3) an aldehyde open chain form; and
  in any of the stereoisomeric and optical isomeric forms thereof.

2. The composition of claim 1, which further comprises a pharmaceutically acceptable carrier.

3. A method of treating a mammal for a condition selected from group consisting of inflammation, pain, hypertermnia and pruritus, which comprises of administering to a mammal in need of such treatment a therapeutically effective amount of the composition of claim 1 for said condition.

4. The method of claim 3 wherein the mammal is a human.

5. The method of 3 wherein the mode of administration is selected from a group consisting of enteral, parenteral, dermal, ocular, nasal, otic, rectal, vaginal, urethral, buccal and pharyngotracheobronchial routes.

6. A process of making the composition of claim 1 which comprises the following steps:
- (a) washing and subsequent freezing of the aerial or vegetable portion of the plant of the family Cactaceae to a temperature between $-10°$ C. and $-33°$ C.;
- (b) thawing said aerial or vegetable portion of the plant to a temperature between $15°$ C. and $20°$ C.;
- (c) trituration of the thawed aerial or vegetable portion of the plant by cutting and impact at between 1000 and 5000 r.p.m.;
- (d) acid digestion of the triturated aerial or vegetable portion of the plant at a temperature between $40°$ C. and $90°$ C.;
- (e) filtering and subsequent neutralization with a hydroxide solution of the acid digested aerial or vegetable portion of the plant to form a filtered solution;
- (f) flocculating with an organic solvent, centrifuging at between 1000 and 2000 r.p.m. and filtering under vacuum said filtered solution to form a residue;
- (g) solubilizing said residue in a mixture of water soluble organic solvent and water in a proportion of (30:70) to (1:99) to form a solubilized residue;
- (h) flocculating with an organic solvent, centrifuging at between 1000 and 2000 r.p.m. and filtering under vacuum said solubilized residue to form a second residue;
- (i) washing the second residue with an organic/aqueous solution in a proportion of (80:20) to (99:1) on a filter support, then drying on a fluidized bed to a temperature between $40°$ C. and $90°$ C. and subsequently sieving said second residue to form a composition, containing a mixture of an aromatic amine and carbohydrates with a particle size between 20 and 1000 microns.

7. A composition derived from a plant of the Cactaceae family, said consists essentially of a mixture of an aromatic amine of formula (R,S)-1-hydroxy-1-(-4-hydroxy-phenyl-)-2-amino-ethane and one or more structural isomers of monosaccharides of galactose and mannose, wherein said monosaccharide is in any one of:
- (1) a pyranoside ring form,
- (2) a furanoside ring form, and
- (3) an aldehyde open chain form; and
  in any of the stereoisomeric and optical isomeric D and L forms thereof.

8. A composition derived from a plant of the Cactaceae family, said consists essentially of a mixture of a disaccharide of formula n1-O-(α,β)-(D,L)-ribofuranosyl-(wα,β)-(D,L)-ribofuranose and at least one structural isomers of monosaccharide of ribose, wherein said monosaccharide is in any one of:
- (1) a pyranoside ring form,
- (2) a furanoside ring form, and
- (3) an aldehyde open chain form; and
  in any of the stereoisomeric and optical isomeric D and L forms thereof.

9. A composition derived from a plant of the Cactaceae family, said consists essentially of a mixture of at least one structural isomer of monosaccharide of glucose, wherein said monosaccharide is in any one of:
- (1) a pyranoside ring form,
- (2) a furanoside ring form, and
- (3) an aldehyde open chain form; and
  in any of the stereoisomeric and optical isomeric D and L forms thereof.

10. A composition derived from a plant of the Cactaceae family, said consists of a mixture of at least one structural isomer of monosaccharide of fucose, wherein said monosaccharide is in any one of:
- (1) a pyranoside ring form,
- (2) a furanoside ring form, and
- (3) an aldehyde open chain form; and
  in any of the stereoisomeric and optical isomeric D and L forms thereof.

11. The composition of claim 7, which further comprises a pharmaceutically acceptable carrier.

12. The composition of claim 8, which further comprises a pharmaceutically acceptable carrier.

13. The composition of claim 9, which further comprises a pharmaceutically acceptable carrier.

14. The composition of claim 10, which further comprises a pharmaceutically acceptable carrier.

15. A method of treating a mammal for at least one condition of inflammation, pain, hypertermia and pruritus which comprises the step of administering to a mammal in need of such treatment a therapeutically effective amount of the composition of any one of claims 7–14 for said condition.

16. The method of claim 15 wherein the mammal is a human.

17. The method of claim 15 wherein the mode of administration is selected from a group consisting of enteral, parenteral, dermal, ocular, nasal, otic, rectal, vaginal, urethral, buccal and pharyngotracheobronchial.

18. A process of making the composition of any one of claims 7–10 which comprises of the steps of:

(a) washing and subsequent freezing of the aerial or vegetable portion of the plant of the family Cactaceae to a temperature between −10° C. and −33° C.;

(b) thawing said aerial or vegetable portion of the plant to a temperature between 15° C. and 20° C.;

(c) trituration of the thawed aerial or vegetable portion of the plant by cutting and impact at between 1000 and 5000 r.p.m.;

(d) acid digestion of the triturated aerial or vegetable portion of the plant at a temperature between 40° C. and 90° C.;

(e) filtering and subsequent neutralization with a hydroxide solution of the acid digested aerial or vegetable portion of the plant to form a filtered solution;

(f) flocculating with an organic solvent, centrifuging at between 1000 and 2000 r.p.m. and filtering under vacuum said filtered solution to form a residue;

(g) solubilizing said residue in a mixture of water soluble organic solvent and water in a proportion of (30:70) to (1:99) to form a solubilized residue;

(h) flocculating with an organic solvent, centrifuging at between 1000 and 2000 r.p.m. and filtering under vacuum said solubilized residue to form a second residue;

(i) washing the second residue with an organic/aqueous solution in a proportion of (80:20) to (99:1) on a filter support, then drying on a fluidized bed to a temperature between 40° C. and 90° C. and subsequently sieving said second residue to form a composition, containing a mixture of an aromatic amine and carbohydrates with a particle size between 20 and 1000 microns;

(j) solubilizing said composition with distilled water by stirring during 1 to 2 hours to form a homogeneous suspension;

(k) centrifuging said homogeneous suspension between 1000 and 2000 rpm to form a solution without particulate matter;

(l) continuous dialysis of said solution without particulate matter, through membranes with molecular weight cut off (MWCO) values below 3500 daltons, to form dialyzed water fractions;

(m) concentration under vacuum of said dialyzed water fraction to form a third residue;

(n) continuous separation by chromatography of said third residue with a mixture of solvent systems, to form different chromatographic fractions;

(o) elution of said chromatographic fractions with water solutions at room temperature to form different solutions;

(p) filtering and subsequent concentration under vacuum of said different solutions; freezing and subsequent lyophilization of said concentrated and filtered solutions to form different residues corresponding to the compositions of said claims 7–10.

* * * * *